(12) United States Patent
Tavares et al.

(10) Patent No.: US 10,557,777 B2
(45) Date of Patent: Feb. 11, 2020

(54) SAMPLING CONTAINER FOR A REMOTELY OPERATED VEHICLE

(71) Applicant: Aquabotix Technology Corporation, Fall River, MA (US)

(72) Inventors: Durval M. Tavares, Fall River, MA (US); Michael Aprea, Plymouth, MA (US)

(73) Assignee: Aquabotix Technology Corporation, Newport, RI (US)

( * ) Notice: Subject to any disclaimer, the term of this patent is extended or adjusted under 35 U.S.C. 154(b) by 168 days.

(21) Appl. No.: 15/882,411

(22) Filed: Jan. 29, 2018

(65) Prior Publication Data

US 2019/0011335 A1   Jan. 10, 2019

Related U.S. Application Data

(60) Provisional application No. 62/457,029, filed on Feb. 9, 2017.

(51) Int. Cl.
| | |
|---|---|
| *G01N 1/12* | (2006.01) |
| *B63G 8/00* | (2006.01) |
| *G01N 1/10* | (2006.01) |
| *B63C 7/00* | (2006.01) |

(52) U.S. Cl.
CPC .............. *G01N 1/12* (2013.01); *B63G 8/001* (2013.01); *B63C 7/00* (2013.01); *B63G 2008/005* (2013.01); *G01N 2001/1025* (2013.01)

(58) Field of Classification Search
CPC . B63G 8/00; B63G 8/001; G01N 1/20; G01N 2001/1031; G01N 1/12; G01N 2001/1025; B63B 25/002; B63B 25/004; B63C 7/00; B63C 7/006
See application file for complete search history.

(56) References Cited

U.S. PATENT DOCUMENTS

| | | | | |
|---|---|---|---|---|
| 3,489,012 | A * | 1/1970 | Niskin | ...................... G01N 1/12 73/863.31 |
| 5,094,113 | A * | 3/1992 | Wood | ........................ G01N 1/12 73/864.67 |
| 5,113,711 | A * | 5/1992 | Davloor | ................... G01N 1/12 73/864.63 |
| 5,341,693 | A * | 8/1994 | Banu | ........................ G01N 1/12 73/864.63 |

(Continued)

*Primary Examiner* — Justin N Olamit
(74) *Attorney, Agent, or Firm* — K&L Gates LLP

(57) ABSTRACT

A sampling container apparatus for a remotely operated vehicle ("ROV") is disclosed. An example sampling container includes a tank configured to hold a sample collected from an underwater environment. The tank includes at least one opening that contains a plunger therein. The plunger includes a contraction or retraction mechanism that pulls the plunger into the tank causing the plunger to actuate from an open position to a closed position. The plunger is retained in the open position by a retainer plate. To enable the plunger to actuate to the closed position, the tank is rotated relative to the retainer plate, causing the plunger to traverse a travel channel in the retainer plate. The travel channel includes a plunger window, which when reached by the plunger, enables the plunger to be pulled through the retainer plate, thereby sealing the opening of the tank and preserving the collected sample.

22 Claims, 17 Drawing Sheets

(56) References Cited

U.S. PATENT DOCUMENTS 6,006,613 A * 12/1999 Dickinson ............... G01N 1/12
73/864.66
8,881,610 B2 * 11/2014 Wulff ...................... G01N 1/12
73/864.63

* cited by examiner

SAMPLING CONTAINER FOR A REMOTELY OPERATED VEHICLE

PRIORITY CLAIM

This application claims priority to U.S. Provisional Application No. 62/457,029, entitled "Liquid Sampling Container for a Remotely Operated Vehicle", filed Feb. 9, 2017, the entire contents of which is incorporated herein by reference and relied upon.

BACKGROUND

Underwater remotely operated vehicles ("ROVs") routinely perform two different types of missions: reconnaissance and sample capture. In reconnaissance missions, an ROV is maneuvered to a particular location so that one or more cameras can record images or video of an intended target. A reconnaissance mission might include an integrity inspection of boat hulls, docks, pipes, water tanks, and other underwater structures. In these types of reconnaissance missions, the recorded images or video are analyzed to locate cracks, bulges, or other signals of structural fatigue and failure. Such missions may require sound and imaging equipment of differing quality and complexity.

In contrast to reconnaissance missions, sample capture missions involve an ROV collecting one or more target objects or fluids for surface-side analysis or disposition. For instance, ROVs may collect underwater sentiment samples, water samples, or aquatic life samples. In some examples, ROVs may even collect lost or forgotten human artifacts, such as pieces from a shipwreck or sunken treasure.

Oftentimes, sample capture containers are bulky and not especially designed for preserving a sample before it is brought to the surface. Some known sample capture containers are nothing more than nets or open boxes, which expose samples to different depths (and possibly damage) when brought to the surface of the water. Other known sample containers include open-ended cylinders or tubes. During operation, these containers collect surface water during an initial plunge, which is not effectively expelled at the sample collection depth. These containers permit water from different locations to be mixed, thereby contaminating the intended sample.

SUMMARY

The present disclosure is directed to a sampling container for an ROV. The example sampling container includes at least one plunger that is placed into an open position prior to the container being used. In some embodiments, each plunger corresponds to a container opening or window leading to an interior tank or chamber where a sample is captured and retained for further use. In other embodiments, one interior tank may include multiple openings that are sealable by a respective plunger. The example sampling container disclosed herein accordingly contains one or more interior tanks or chambers with corresponding plungers.

The plungers of the example sampling chamber disclosed herein are held in an open position by a retainer plate. While underwater, the sampling container is configured to collect a sample in an interior tank or chamber through one or more openings or windows made accessible by the plunger(s) being in an open position. After a sample is collected, the sampling container is rotated relative to the retainer plate. After sufficient rotation, the plunger(s) reaches an opening (e.g., a plunger window) in the retainer plate, which enables a constriction or a retraction mechanism (e.g., a spring, an elastic band, etc.) of the plunger(s) to pull the plunger(s) toward a respective opening in the interior tank or chamber, thereby enabling the plunger(s) to actuate to a closed position. Each of the openings to the interior tank or chamber is sealed when the plunger(s) are pulled to the closed position. Sealing the interior tank or chamber preserves the collected sample from contamination or dilution.

As disclosed herein, the interior tank or chamber may include one or more openings at one end or both ends. In instances where the tank or chamber includes openings at both ends, a single plunger, with cups at each end, may be used to seal opposing openings. In other examples, a separate plunger may be used for each opening at each end of the tank or chamber of the sampling container.

In an example embodiment, a sampling container apparatus includes a motor housing comprising a motor configured to rotate a at least one magnet around a drift shaft of the motor and a magnetic plate configured to magnetically couple to the at least one magnet of the motor housing. The magnetic plate is configured to rotate in unison with the at least one magnet of the motor housing. The a sampling container apparatus also includes a shroud housing configured to enclose at least some of the motor housing and the magnetic plate and a sample container housing configured to be placed within the shroud housing and mechanically connected to the magnetic plate. The sample container housing includes a tank configured to hold a sample within an interior chamber. The tank includes a first end having a first opening to the interior chamber and a second end having a second opening to the interior chamber. The ample container housing also includes a plunger having a shaft positioned within the interior chamber. The plunger has a first cup at a first end configured to seal the first opening of the tank and a second cup at a second end configured to seal the second opening of the tank. The shaft of the plunger is connected to the first end and the second end of the plunger and configured to pull the first end and second end of the plunger towards each other.

The example sampling container apparatus further includes a first retainer plate located above the first end of the sample container housing and a second retainer plate located below the second end of the sample container housing. The first retainer plate includes a first plunger window configured to enable the first cup of the plunger to pass through and a first travel channel connected to the first plunger window. The first travel channel has a diameter that is larger than the shaft and smaller than the first cup of the plunger. The second retainer plate includes a second plunger window configured to enable the second cup of the plunger to pass through and a second travel channel connected to the second plunger window. The second travel channel has a diameter that is larger than the shaft and smaller than the second cup of the plunger. The first and second retainer plates are configured to retain the plunger in an open position until the sample container housing is rotated by the motor, causing the sample container housing including the plunger to rotate relative to the first and second retainer plates along the first and second travel channels such that the first cup passes through the first plunger window and the second cup passes through the second plunger window when the cups are aligned with the respective windows, thereby enabling the plunger to actuate to a closed position and causing the first cup to seal the first open opening of the tank and the second cup to seal the second opening of the tan In another example embodiment, a sampling container apparatus includes a motor housing comprising a motor configured to rotate a drive shaft and a sample container housing rotatably connected to the motor housing via the drive shaft. The sample container housing includes a first end connected to the drive shaft of the motor, a second end located opposite the first end, an interior tank configured to hold a sample, a container window located at the second end, a channel positioned between the container window and the interior tank, and a spring-loaded plunger having a shaft positioned within the channel and a cup located at an end of the shaft in proximity to the container window. The example sampling container apparatus also includes a retainer plate located above the second end of the sample container housing. The retainer plate includes a plunger window configured to enable the cup of the plunger to pass through and a travel channel connected to the plunger window, the travel channel having a diameter that is larger than the shaft and smaller than the cup of the plunger. The sampling container apparatus additionally includes a shroud housing configured to enclose the motor housing and the sample container housing. The retainer plate holds the spring-loaded plunger in an open position until the sample container housing is rotated by the motor, causing the sample container housing including the plunger to rotate relative to the retainer plate such that the cup passes through the plunger window enabling the spring-loaded plunger to actuate to a closed position, thereby causing the cup to cover the container window and seal access to the interior tank.

The advantages discussed herein may be found in one, or some, and perhaps not all of the embodiments disclosed herein. Additional features and advantages are described herein, and will be apparent from the following Detailed Description and the figures.

DETAILED DESCRIPTION

Figure 1:
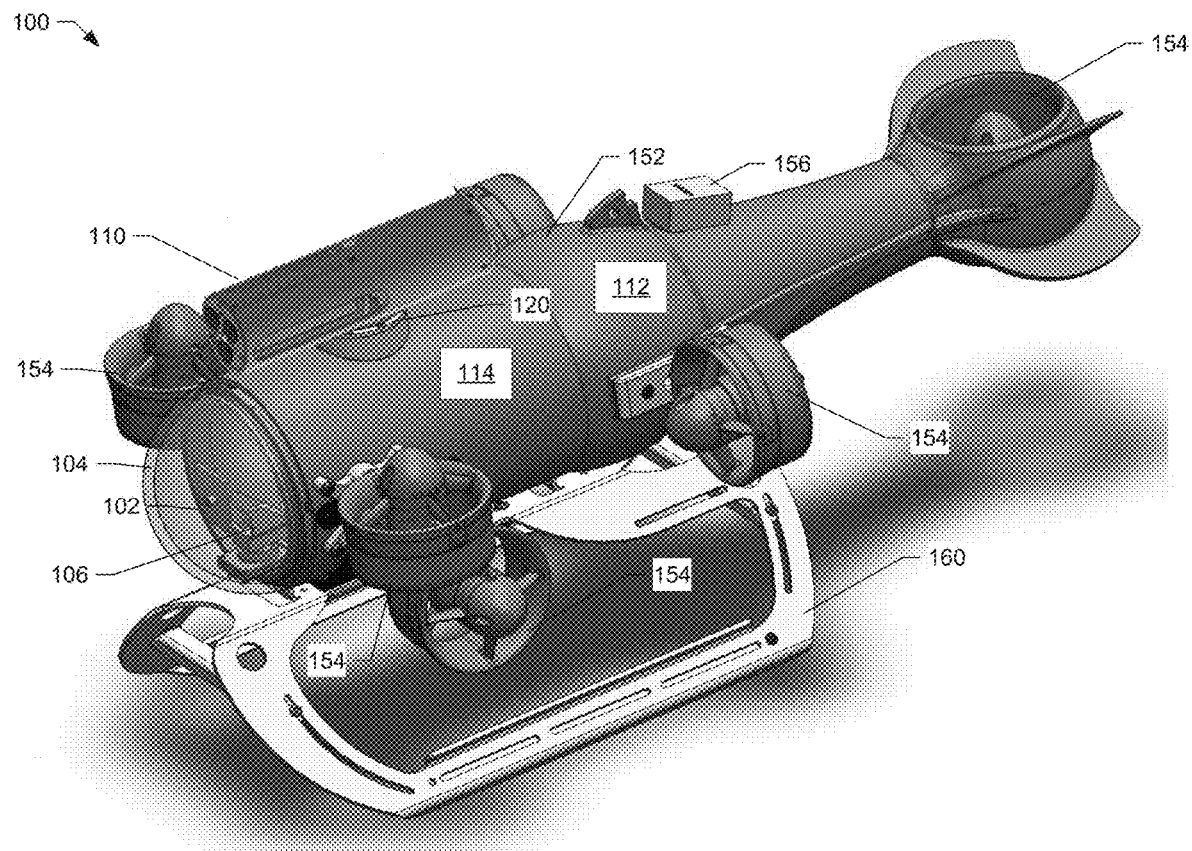
FIGS. 1 and 2 and show diagrams that illustrate an ROV with a sampling container, according to embodiments of the present disclosure.

The present disclosure relates in general to a sampling container that is sealable underwater. The example sampling container is attachable to an underwater remotely operated vehicle ("ROV"), an autonomous underwater vehicle ("AUV"), or more generally, an unmanned underwater vehicle ("UUV"). During use, an operator moves the ROV or programs the AUV to move to a desired location where a sample is to be collected. After a sample is placed in the example container or otherwise collected in the container, the operator remotely closes the sampling container to preserve the integrity of the sample. For AUV's, an onboard controller may cause the sampling container to close after sample collection is detected or otherwise determined.

In some embodiments, the sampling container may be connected to a robotic arm or other appendage of the ROV/AUV/UUV. In these embodiments, the robotic arm moves the sampling container to a desired location to collect a sample, which may include any fluid sample, sentiment sample, biological sample, sunken human artifacts, etc. For example, a sample may comprise oil mixed with water, natural gas mixed with water, underwater volcanic discharge, coral spawning, fresh water, salt water, etc.

The example sampling container disclosed herein includes one or more windows or openings that enable a sample to be collected in an interior tank or chamber. A plunger with a cup is provided in each window or opening. Before use, the plunger is placed into an open position. During sample acquisition, the plunger is actuated or otherwise permitted to retract, thereby causing the cup to cover and/or seal the respective window. The closing of the plunger forms a relatively tight seal between the cup and the respective window, thereby preventing the sample from escaping or becoming contaminated during the reminder of a mission.

The example sampling container uses one or more retainer plates that provide for plunger control. Before use, at least a portion of the plungers are placed into an open position by being placed on the one or more retainer plates, which prevents the plungers from retracting. While underwater, the sampling container collects a sample through the one or more windows or openings. In some instances, windows or openings may be placed on both sides of a sample container to enable water or other fluids to more easily flow through for collection in an interior tank or chamber.

After a sample has been collected, a motor is activated, which rotates the sampling container and the one or more plungers with respect to the stationary retainer plate(s). The example retainer plate(s) includes at least one opening or window that enables the one or more plungers (or portion thereof) to pass through. Rotation of the sampling container and plungers causes the plungers to move toward the window or opening in the retainer plate(s). When the plunger reaches the opening in the retainer plate(s), the plunger is able to retract, thereby pulling the plunger through the opening of the retainer plate towards the interior tank or chamber. As a result of the retractile or contractive force of the plunger, a cup of the plunger is configured to contact a perimeter of the window of the sampling container causing the window to be covered and sealed. Once all the plungers have moved to a closed position, all of the chambers of the sampling container are sealed from the outside environment.

The example plunger includes a retraction and constriction mechanism to cause them to retract or otherwise pull toward an interior of a chamber or tank. The retraction and constriction mechanism may include an elastic or rubber band. The retraction and constriction mechanism may also include a spring. Additionally, the retraction and constriction mechanism may include a magnetic coupler or mechanically assembly that is configured to apply a pulling or restrictive force to the plunger.

The example sampling container enables samples of water or other liquids to be collected at a particular location without the samples becoming tainted when the sampling container (and the ROV/AUV/UUV) moves to another location or the surface. The use of the plungers provides a relatively compact design that enables the example sampling container to be used in tight locations underwater.

In contrast to the example sampling container disclosed herein, known sample containers with lids need sufficient room for the lid to be opened and closed, which usually includes rotating the lids around a hinge. Furthermore, the example sampling container disclosed herein requires few moving parts: only components for rotating the sampling container relative to the retainer plate and components for the contraction of the plungers. Thus, the example sampling container disclosed herein is relatively easy to manufacture and assemble, which reduces the cost of the sampling container assembly. In addition, the design and lack of moving parts mitigates the risk that environmental factors inhibit the functionality of the sampling container. Furthermore, the example sampling containers enable multiple samples to be obtained from various locations, while preserving the integrity of the earlier collected samples.

The example sampling container disclosed herein is also reusable, which provides value to end-users. For example, after a sample has been extracted, the sampling container may be washed or otherwise sterilized. In addition, the plungers of the example sampling container may be returned to open positions by pulling the plungers through the retainer plate(s) while rotating the retainer plates.

Reference is made throughout to underwater ROVs. It should be appreciated that the disclosed sampling container apparatus is not limited to underwater vehicles. For example, the disclosed sampling container apparatus may be part of an above-water ROV or manned boat. In other embodiments, the disclosed sampling container apparatus may be included on an unmanned aerial vehicle ("UAV"), drone, airplane, high altitude platform, or any other device that operates from a battery. Furthermore, the sampling container apparatus can be configured to operate in a vacuum, which allows for the sampling container apparatus to be used in extra-atmospheric near extra-atmospheric conditions such as low-earth orbit.

Example ROV/AUV/UUV

FIG. 1 shows a diagram illustrating an ROV 100 that includes a sampling container 110, according to an example embodiment of the present disclosure. The ROV 100 may include any type of vehicle including an AUV or UUV. The ROV 100 of FIG. 1 is configured to operate underwater to collect samples from one or more locations in the sampling container 110. The ROV 100 includes a housing or body 152 (e.g., a hull) configured to enclose control electronics, power electronics, and a power supply including one or more batteries 112, or any combination of these or other components. The electronics or power supply may control, for example, rotation rates and timing of propellers 154. In addition, the electronics or power supply may control a motor within the sampling container 110.

As shown in FIG. 1, the sampling container 110 may be externally mounted or otherwise affixed to the ROV 100 via a connection mechanism 120. Such a configuration enables water or other fluids to pass through a collection or interior tank/chamber. It should be appreciated that the sampling container mounting location is not limited to the position shown in FIG. 1. In other embodiments, the sampling container 110 is connected to an appendage or robotic arm of the ROV 100. Such a configuration enables the robotic arm to change an orientation of the sampling container 110 to improve sample collection. The robotic arm may also enable the sampling container 110 to be placed in proximity of a liquid of interest in which it is not feasible or safe to bring the ROV 100 closer. In some instances, the sampling container 110 may operate with the robotic arm such that the arm deposits sentiment or biological samples into the container 110.

In yet other embodiments, the sampling container 110 may be connected to another portion of the ROV, such as at a belly of the housing 152 or connected to landing gear 160. Moreover, in some embodiments, the ROV 100 may be integrally formed and/or at least partially enclosed by the body 152 of the ROV 100. Furthermore, since most ROVs are capable of multi-directional motion, the orientation of the sampling container need not be oriented in any particular direction relative to the ROV 100.

In further embodiments, the sampling container 110 may be connected to the ROV 100 via a tether. In these further embodiments, the sampling container 110 may be towed behind the ROV 100. The tether may provide signals or power to the sampling container 110.

In still other embodiments, the sampling container 110 may be removably attached to the ROV 100. For example, the connection mechanism 120 may include magnetic plates or a detachable connector that enable the sampling container 110 to be removed. Alternatively, the connection mechanism 120 may include threads or screws that enable the sampling container 110 to be detached from the body 152 of the ROV 100.

In some embodiments, the example sampling container 110 is electrically connected to the one or more batteries 112 to power an internal motor. Additionally or alternatively, the sampling container 110 is electrically connected to control electronics 114. The control electronics 114 are configured to provide signals for operating one or more motors to close or otherwise seal the sampling container 110 after a sample has been collected. The control electronics 114 also provide electrical signals for operating propellers 154. In some embodiments, the control electronics 114 comprise a transceiver to communicate with a surface workstation, or processors for receiving, formatting, and storing images or video from cameras or receiving operational instructions (e.g., an instruction to close the sampling container 110). The control electronics 114 may, for example, cause the sampling container 110 to transition from an open position or state to a closed position or state once a sample has been collected. In some examples, the control electronics 114 may automatically determine that the sampling container 110 is to be closed based on being within a specified location for a specified duration of time. In other examples, the control electronics 114 may receive a signal from the surface indicating that the sampling container 110 is to be closed. In still other examples, the control electronics 114 may be configured to determine the sampling container 110 is to be closed upon the occurrence of a specified value from another sensor on the ROV 100, such as a measured temperature, pressure, flow, or sunlight intensity value.

In some embodiments, the sampling container 110 may include more than one interior tank or chamber for sample collection. In these embodiments, the control electronics 114 may transmit signals causing only one or a few of the available tanks or chambers to seal. For example, after collecting a water sample at a first location, the control electronics 114 cause a first chamber of the sampling container 110 to seal. Then, after collecting a water sample at a second different location, the control electronics 114 cause a second chamber of the sampling container 110 to seal. Such a configuration enables samples from different locations and/or different samples to be collected during the same underwater mission.

The control electronics 114 are communicatively coupled to a surface workstation (e.g., a computer or smartphone operating an application) via one or more wires connected to a junction box 156. The wires may comprise Ethernet-compatible wires, USB-compatible wires, or HDMI-compatible wires that enable a high speed data connection between the ROV 100 and a surface workstation. In one example, the wires may carry image data recorded by a camera, and transmitted by a transceiver. The wires may also carry signals comprising sensor data or diagnostic information (such as which propellers are active and/or rotation rate). The wires may also provide feedback, such an indication that the sampling container 110 has been closed (or which chambers on the sampling container 110 have been sealed), based on the control electronics 114 detecting a rotation amount of a motor drive shaft within the sampling container 110.

The wires are also configured to receive commands from the surface workstation. The commands may include, for example, control commands that cause the control electronics 114 to activate one or more propellers 154, move the ROV 100 in a specified direction and a specified speed, and/or to close the sampling container 110 (or one or more chambers of the sampling container 110). The commands may also update mission information, remove missions, add missions, or provide an indication of a mission being completed. The commands may further include configuration information that specify or change how certain devices on the ROV 100 operate. For example, configuration information may change a sensor sampling rate, deactivate a sensor, or change a brightness of a lighting device. In other examples, the commands may contain contingency information, such as instructions for the ROV 100 to surface if communication is lost for a pre-determined amount of time.

The body 152 of FIG. 1 also includes a front compartment 104, which encloses a camera 102 and camera support 106. The example camera 102 may be used for navigating the ROV 100 or providing a forward facing view. In some examples, the ROV 100 may include a rotatable camera apparatus with corresponding lighting device, as described in U.S. patent application Ser. No. 15/814,096, titled "Remotely Operated Vehicle Camera Apparatus," the contents of which are incorporated herein by reference.

Figure 2:
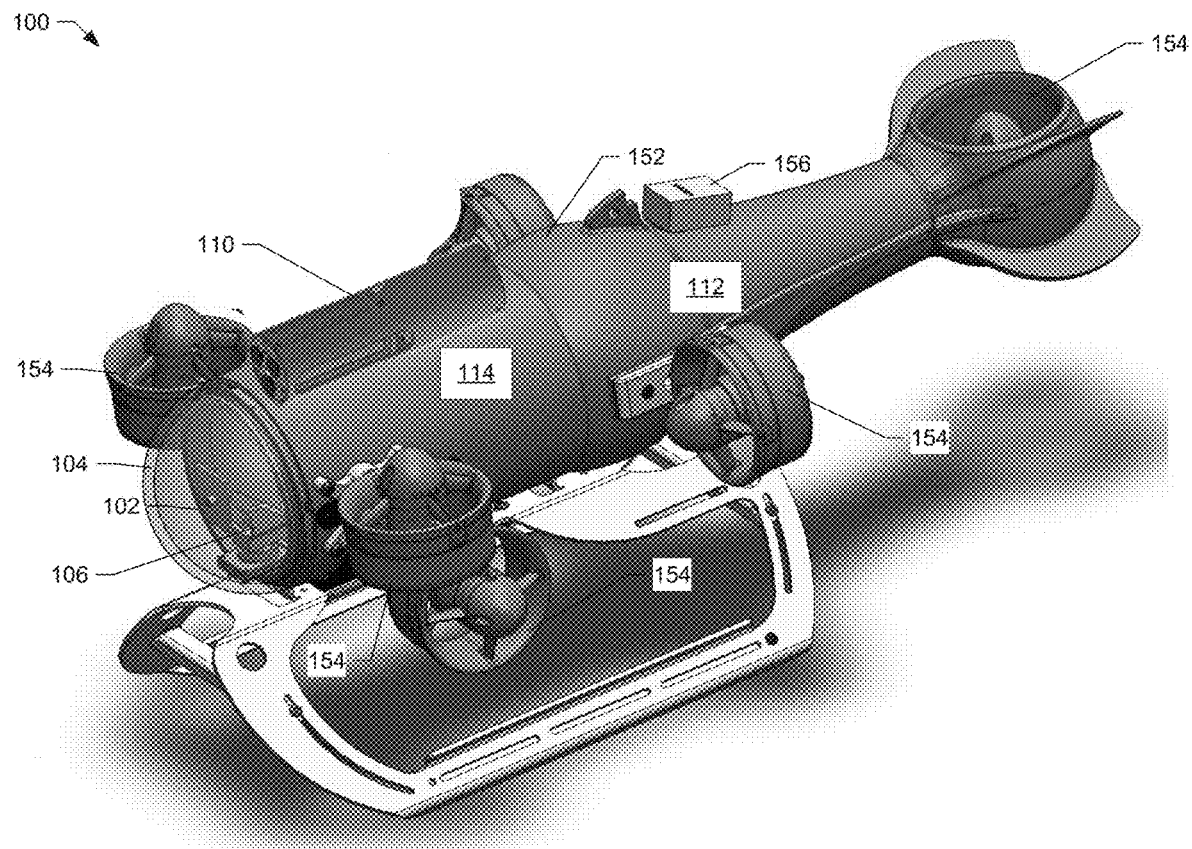

FIG. 2 shows an alternate embodiment where the sampling container 110 is integrated into the housing 152. In the illustrated example, the sampling container 110 is located at the top of the housing 152 oriented in a horizontal orientation. In other examples, the sampling container 110 may be integrated at other locations, such as a side or belly of the ROV 100.

While the examples in FIGS. 1 and 2 show a single sampling container 110, it should be appreciated that the ROV 100 may include two or more sampling containers 110. Further, while the sampling container 110 has been shown in a horizontal orientation, in other embodiments, the sampling container 110 may be provided at an angled or vertical orientation with respect to the ROV 100. Further, while the sampling container 110 is shown as being a circular cylinder, it should be appreciated that a profile of the sampling container 110 may comprise other profiles, such as an oval, a square, a rectangle, a pentagon, or a hexagon.

First Embodiment of the Example Sampling Container

Figure 3:
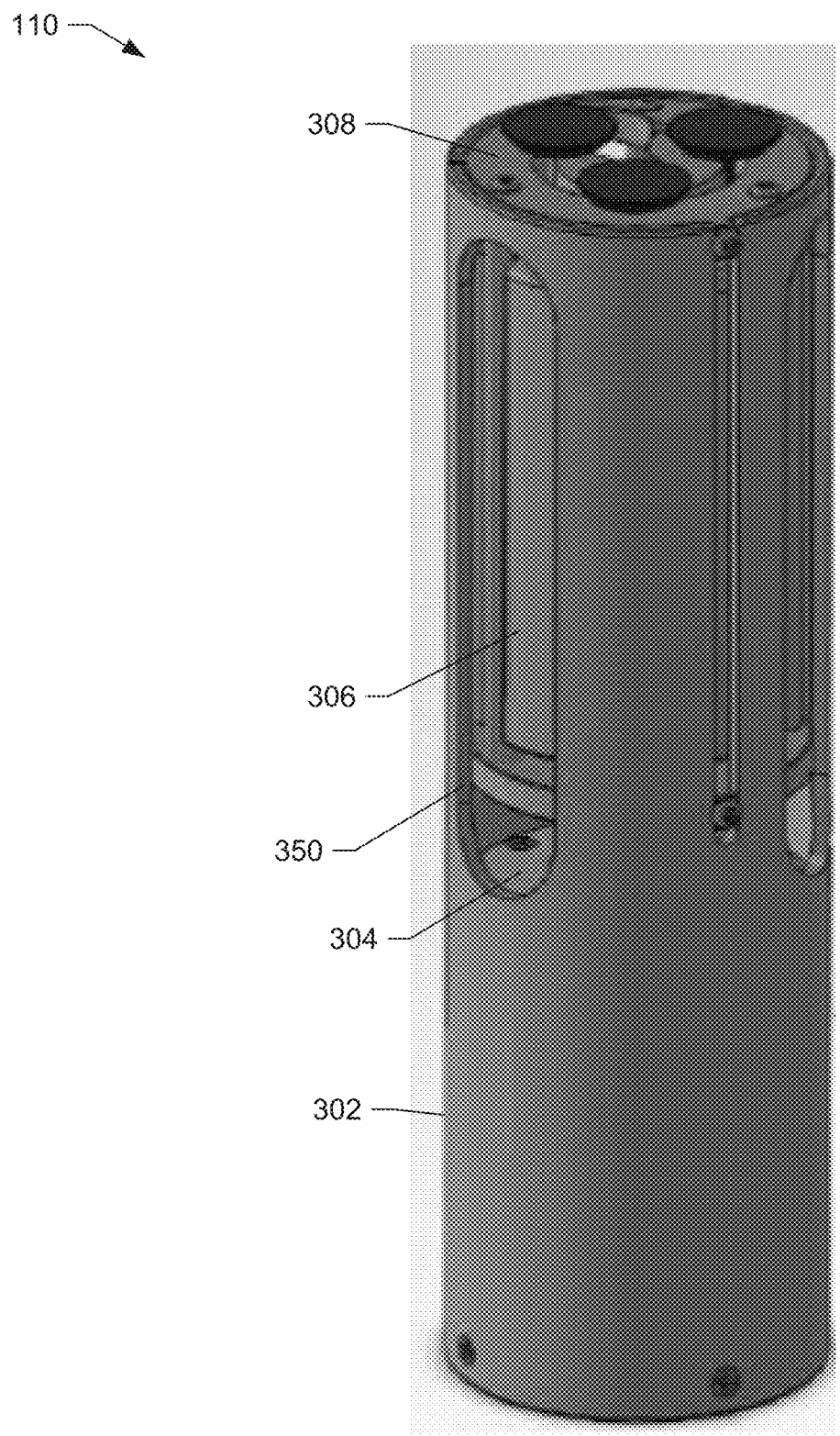
FIG. 3 shows a diagram of the sampling container of FIGS. 1 and 2, according to embodiments of the present disclosure.
Figure 4:
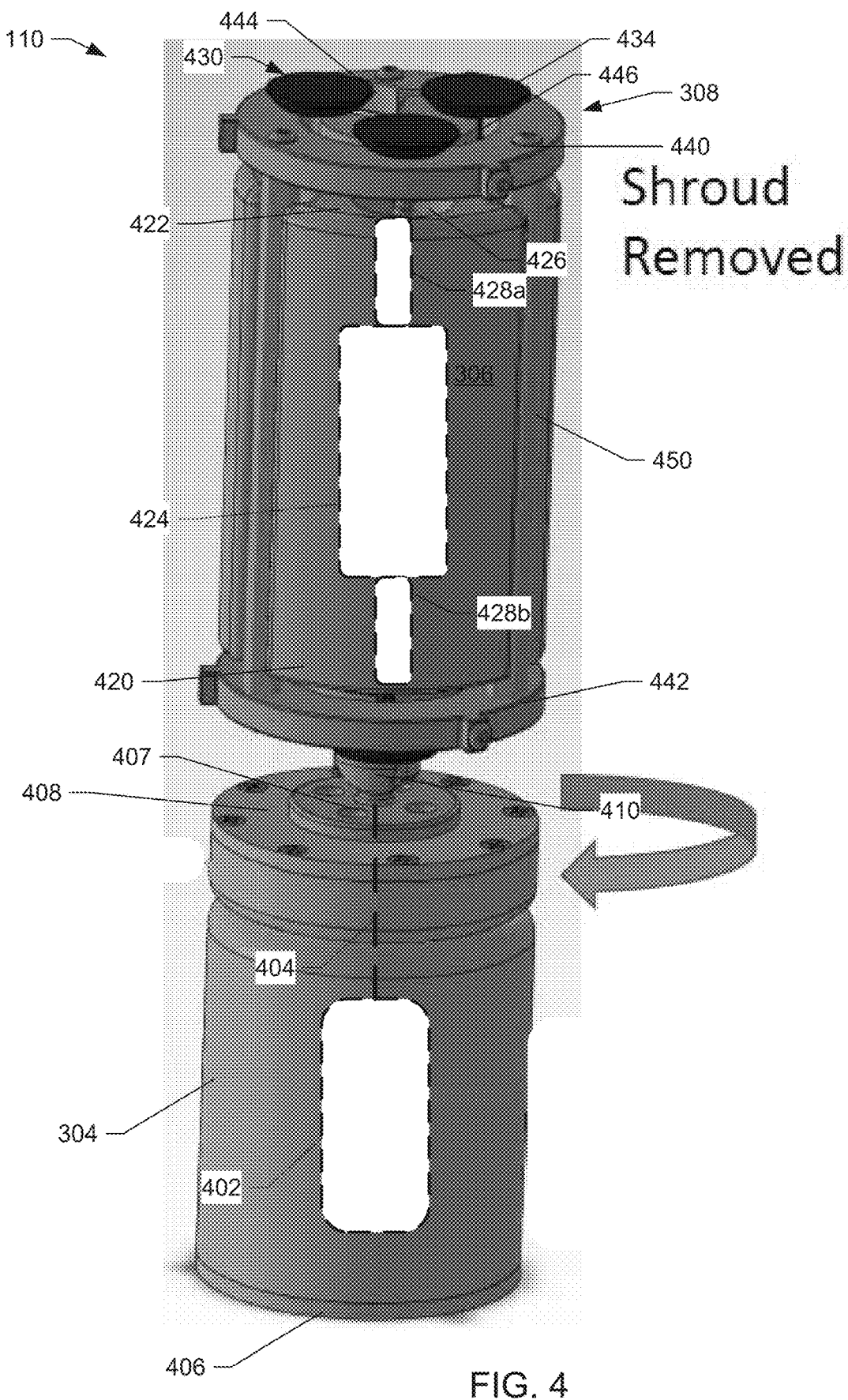
FIG. 4 shows a diagram of the sampling container of FIGS. 1 and 2 with the shroud housing removed, according to an embodiment of the present disclosure.
Figure 5:
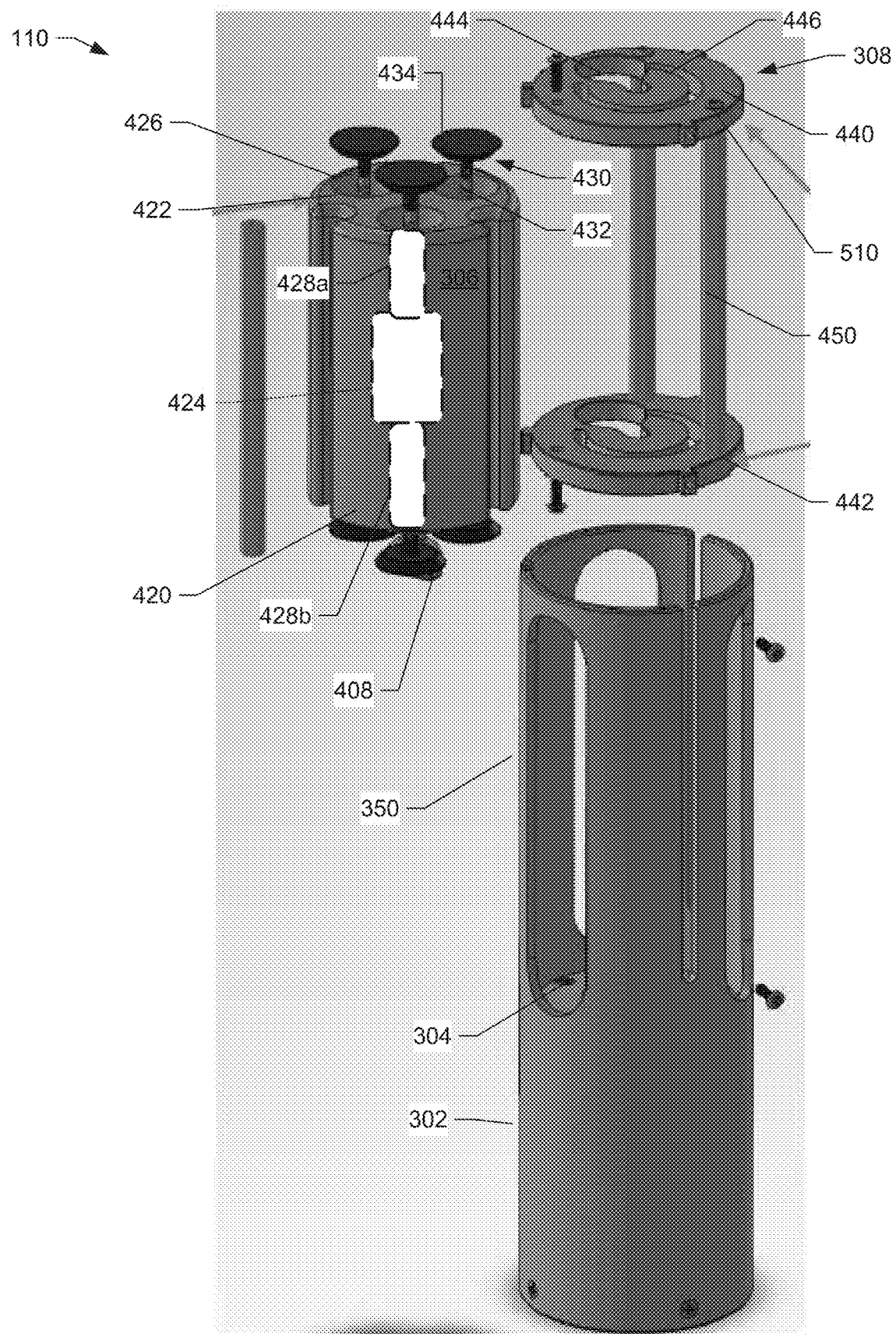
FIG. 5 shows an assembly view of the sampling container of FIGS. 1 and 2 where the sample container housing is removed from the shroud housing, according to an embodiment of the present disclosure.

FIGS. 3 to 8 are diagrams that illustrate a first embodiment of the sampling container 110 of FIGS. 1 and 2. FIG. 3 shows a diagram with a shroud housing 302 of the sampling container 110 in place while FIG. 4 shows a diagram with the shroud housing 302 removed. FIG. 5 shows an assembly view of the sampling container 110.

The example shroud housing 302 shown in FIG. 3 is configured to contain a motor housing 304, a sample container housing 306, and a retainer plate 308. The example motor housing 304, shown in FIGS. 3 to 5, is located at a first side of the shroud housing 302 and configured to rotate the sample container housing 306. The motor housing 304 is substantially enclosed by the shroud housing 302.

The example shroud housing 302 may include one or more windows 350 that enable water to pass through to the sample container housing 306. The windows 350 may comprise any shape, dimension, or proportion relative to the sample container housing 306. In addition, windows 350 shown here are distributed evenly throughout the circumference of the shroud housing 302. However, windows 350 may be distributed in any manner across or throughout the shroud housing 302. For example, windows 350 may be a stamped pattern in the shroud housing 302. Such a stamped pattern would allow for liquid to flow easily across the shroud housing 302 to be collected in the sample container housing 306, but would still provide a rigid structure and ample protection for the components of the sampling container 110 within the shroud housing 302.

As shown in FIG. 4, the motor housing 304 includes a motor 402 configured to rotate a drive shaft 404. The motor 402 may receive power (and/or control signals) via an electronic coupling at a side 406 of the motor housing 304. For instance, power wires may be routed from the side 406 to the battery 112 via the housing 152 of the ROV 100. In other examples, the motor housing 304 may include a battery to provide power to the motor 402. Additionally or alternatively, one or more control wire may be routed from the side 406 to the control electronics of the ROV 100.

The motor 402 is configured to operate according to one or more signals. For example, the motor 402 may operate at a speed and/or duration specified within a pulse width modulation signal transmitted from the control electronics 114. In some instances, the signals may be provided wirelessly. For example, the signals may be provided via a near field communication, Bluetooth®, or Zigbee® connection, or any combination thereof.

The drive shaft 404 of the illustrated example is connected to a ring 407, which is rotatably connected to a lid 408 of the motor housing 304. The drive shaft 404 causes the ring 407 to rotate while the ring 407 forms a water-tight connection with the lid 408. The water-tight connection prevents water from entering an inside of the housing 304 and affecting operation of the motor 402.

The example sample container housing 306 is configured to connect to the ring 407 of the motor housing 304 via a connector 410. The example connector 410 may include screw threads that couple with corresponding threads on the ring 407. Alternatively, the connector 410 may engage the ring 407 via a snap coupling or pressure coupling. In addition, the connector 410 may be configured to be removably connected to the ring 407, causing the sample container housing 306 to be removable from the sampling container 110. Removing the sample container housing 306 at the completion of a mission enables relatively easy sample removal since the sample container housing 306 is less cumbersome during sample retrieval than the entire sampling container 110.

As shown in FIG. 4, the example sample container housing 306 includes a first end 420, which comprises the connector 410. The sample container housing 306 also includes a second end 422 opposite of the first end 420. Between the ends 420 and 422, the example container sample housing 306 includes an interior tank 424 (e.g., a sample collection tank/chamber) configured to store one or more sample upon collection. At least one of the ends 420 and 422 includes a container window 426 (e.g., an opening to the tank 424) and a channel 428 positioned between the window 426 and an interior of the tank 424. The container window 426 and channel 428 provide a passage or pathway for a sample to travel from an outside of the sample container housing 306 to the interior tank 424.

The embodiment shown in FIGS. 3 to 5 illustrates that each of the ends 420 and 422 includes three container windows 426 and corresponding channels 428 (e.g., channels 428a and 428b that are fluidly coupled to tank 424). In other examples, the ends 420 and 422 may include fewer or additional windows with fewer or additional corresponding channels. Moreover, in some examples, only one of the ends 422 or 422 may include one or more container windows 426. However, it should be appreciated that having container windows 426 at both of the ends 420 and 422 enables water or other liquids to pass through the tank 424 and channels 428a and 428b. This enables, for example, the sampling container 110 to collect a liquid that is indicative of a sample location rather than a mixing of different liquids encountered along a mission. For instance, having a container window 426 at only one of the ends 420 or 422 results in the tank 424 accumulating water soon after the sampling container 110 is submerged. Once the tank 424 fills with water upon the initial submersion of the sampling container 110, the water becomes trapped because the water is not able to easily flow from the tank, thereby making it more difficult to obtain a sample later during the mission without some effect to the sample from the previously trapped water.

The example sample container housing 306 includes a plunger 430 for each container window 426 and channel 428. Each plunger 430 includes a shaft 432 positioned within the channel 428. Each plunger 430 also includes a cup 434 located at an end of the shaft 432 in proximity to the respective container window 426. The shaft 432 includes or is coupled to a spring or elastic band, which is configured to pull the shaft toward a center of the sample container housing 306 (or into a center of tank 424). In some instances, the springs or bands may be connected to a support within the tank 424 or adjacent to the tank 424. The springs or bands are configured to provide a constrictive or retractile force on the respective plunger 430, which causes the cup 434 to create a water-tight seal with the container window 426 when the plunger 430 is pulled to a closed position.

In some embodiments, opposing plungers 430 may be mechanically connected together or otherwise integrated. For example, a plunger 430 through channel 428a may be connected to or integrally formed with a plunger 430 through channel 428b. Specifically, shafts 432 of the plungers 430 are connected together or integrally formed. In some examples, the shafts 432 include a constriction mechanism, and a retraction mechanism that pulls the plungers 430 of the channels 428a and 428b toward each other (which is towards a center of tank 424). The constriction mechanism or a retraction mechanism may include a spring, an elastic band, magnetic couplers, weighted rods, etc.

The example sampling container 110 includes retainer plates 308 to retain or hold the plungers in an open position. In the illustrated example, the retainer plate 308 includes a top plate 440 and a bottom plate 442 corresponding to the plungers 430 located at each of the sides 420 and 422 of the sample container housing 306. In instances where only one end 420 or 422 has a container window 426, the retainer plate 308 may only have the top plate 440 or bottom plate 442.

Each of the plates 440 and 442 includes a plunger window 444 and a travel channel 446. The plunger window 444 is dimensioned to enable the cup 434 of the plunger 430 to pass through when the cup 434 is aligned with the window 444. The travel channel 446 has a diameter that is less than the cup 434 but greater than the width of the shaft 432, which retains the plunger 430 in an open position. The channel 446 is shaped to conform to a rotation of the sample container housing 306 to enable the shafts 432 of the plungers 430 to rotate unimpeded through the plates 440 or 442. When the shafts 432 reach the respective window 444, the window 444 is wide enough to enable the respective cup 434 to pass through, thereby enabling the plunger 430 to move from the open position to the closed position.

Figure 6:
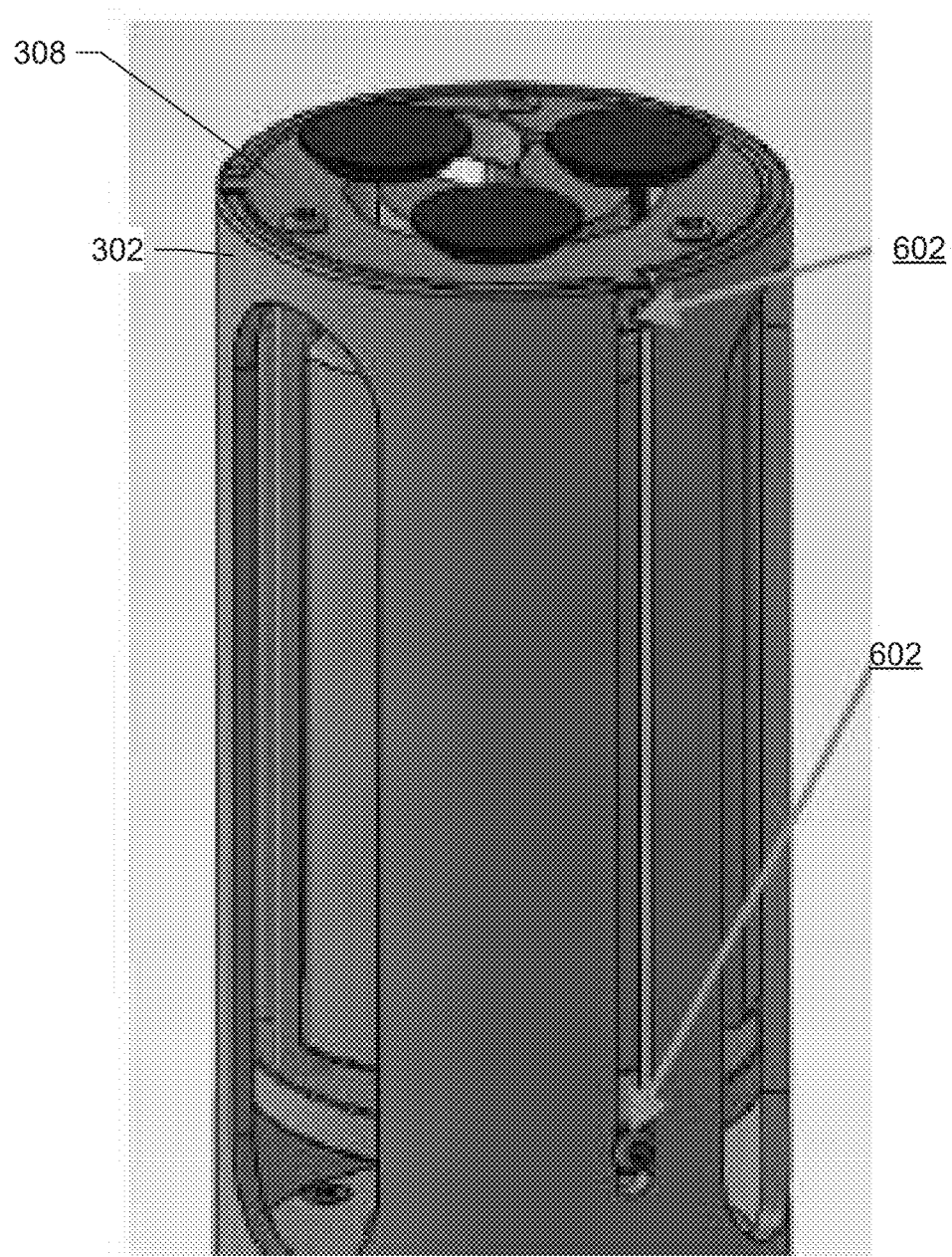
FIG. 6 shows a diagram of the sampling container of FIGS. 1 and 2 with plungers in an open position, according to an embodiment of the present disclosure.

Each of the plates 440 and 442 are mechanically coupled to the shroud housing 302 such that the retainer plates 440 and 442 are fixed in place. For example, screws 602 (as shown in FIG. 6) may couple the retainer plate 308 to the shroud housing 302. However, coupling the shroud housing 302 to each of the plates 440 and 442 can be accomplished through other means, such as snaps, fasteners, or bolts, so long as the retainer plate 308 remains fixed when the motor 402 is actuated.

The example plates 440 and 442 are coupled together via one or more support beams 450. The support beams 450 may ensure that the plates 440 and 442 are aligned with each other. The support beams 450 may also provide some rigidity to the plates 440 and 442. Support beams 450 may be attached to a retainer plate 308 using one or more connectors. Here, support beams 450 are attached to plates 440 and 442 using two exemplary fasteners. The first fastener 510 includes a screw used to connect a support beam 450 to the plates 440 and 442. The second fastener includes a screw and washer combination used to connect a support beam 450 to the plates 440 and 442. Alternatively, the support beam 450 and retainer plate 440 or 442 may be manufactured from a single component or integrally formed.

Figure 7:
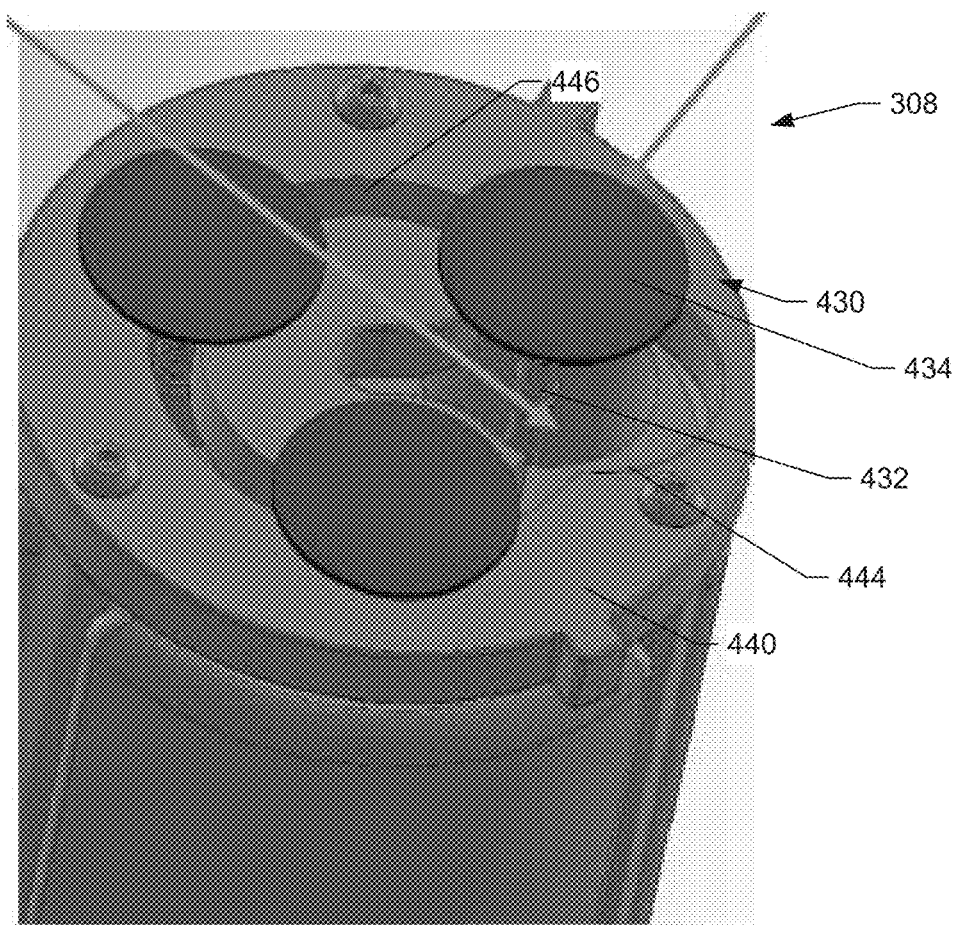
FIG. 7 shows a diagram of the sampling container of FIGS. 1 and 2 with the shroud housing removed and with the retainer plate still in place, according to an embodiment of the present disclosure.
Figure 8:
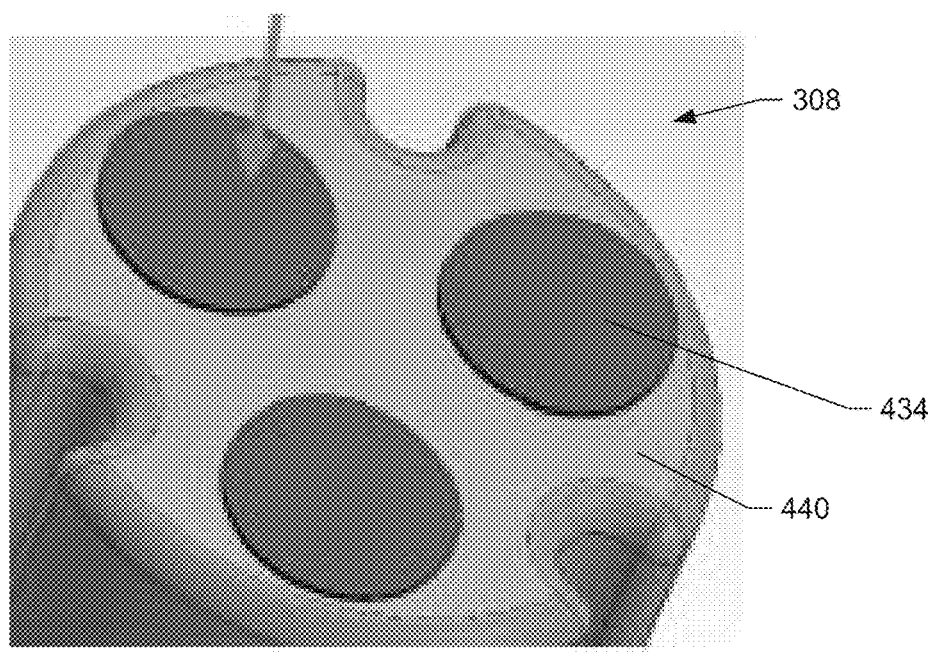
FIG. 8 shows a diagram of the sampling container of FIGS. 1 and 2 with the shroud housing removed and with the retainer plate removed, according to an embodiment of the present disclosure.

As shown in FIGS. 4, 5, 6 and 7, the retainer plate 308 is configured to retain or hold the plungers 430 in an open position prior to a sample being collected. In other words, the cups 434 rest on top of the channel 446, which prevents the spring or band of the plunger 430 from pulling the shaft 432 any further downward into the tank 424. Then, when the motor 402 is actuated, the sample container housing 306 rotates relative to the retainer plate 308. The plungers 430 move with the sample container housing 306 such that they move through or within the channel 446 defined by an opening in the plates 440 and 442. Eventually, during rotation a plunger 430 reaches the plunger window 444 (as shown in FIG. 7), at which point the force of the spring or band causes the plunger 430 to pull the cup 434 downward through the window 444 to cover the container window 426. If the motor 402 continues to operate, soon afterwards, the cups 434 of the other plungers 430 sequentially reach the window 444 and likewise actuate to a closed position. At this point, the sample container housing 306 is sealed (as shown in FIG. 8, with the retainer plate 308 omitted for ease of viewing).

Second Embodiment of the Example Sampling Container

Figure 9:
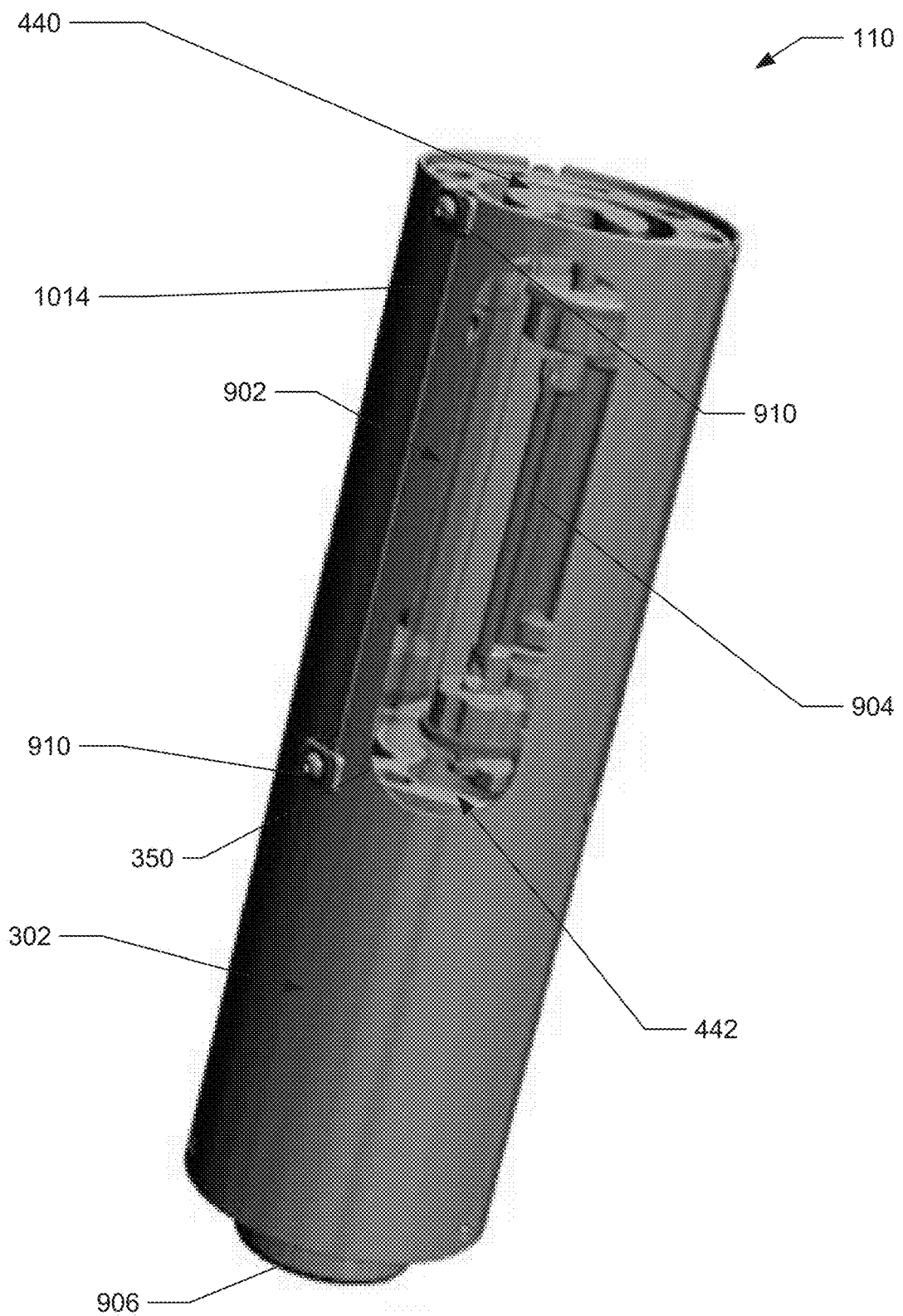
FIG. 9 shows a diagram of a second embodiment of the sampling container.

FIGS. 9 to 16 are diagrams that illustrate a second embodiment of the sampling container 110 of FIGS. 1 and 2. FIG. 9 shows a diagram of the sampling container 110 with a sample container housing 902 comprising a transparent material. Combined with windows 350 in shroud housing 302, the transparent material of the sample container housing 902 enables an operator and/or a sensor to view contents of tank 904. The sample container housing 902 is rotated by a motor housing 906.

Figure 10:
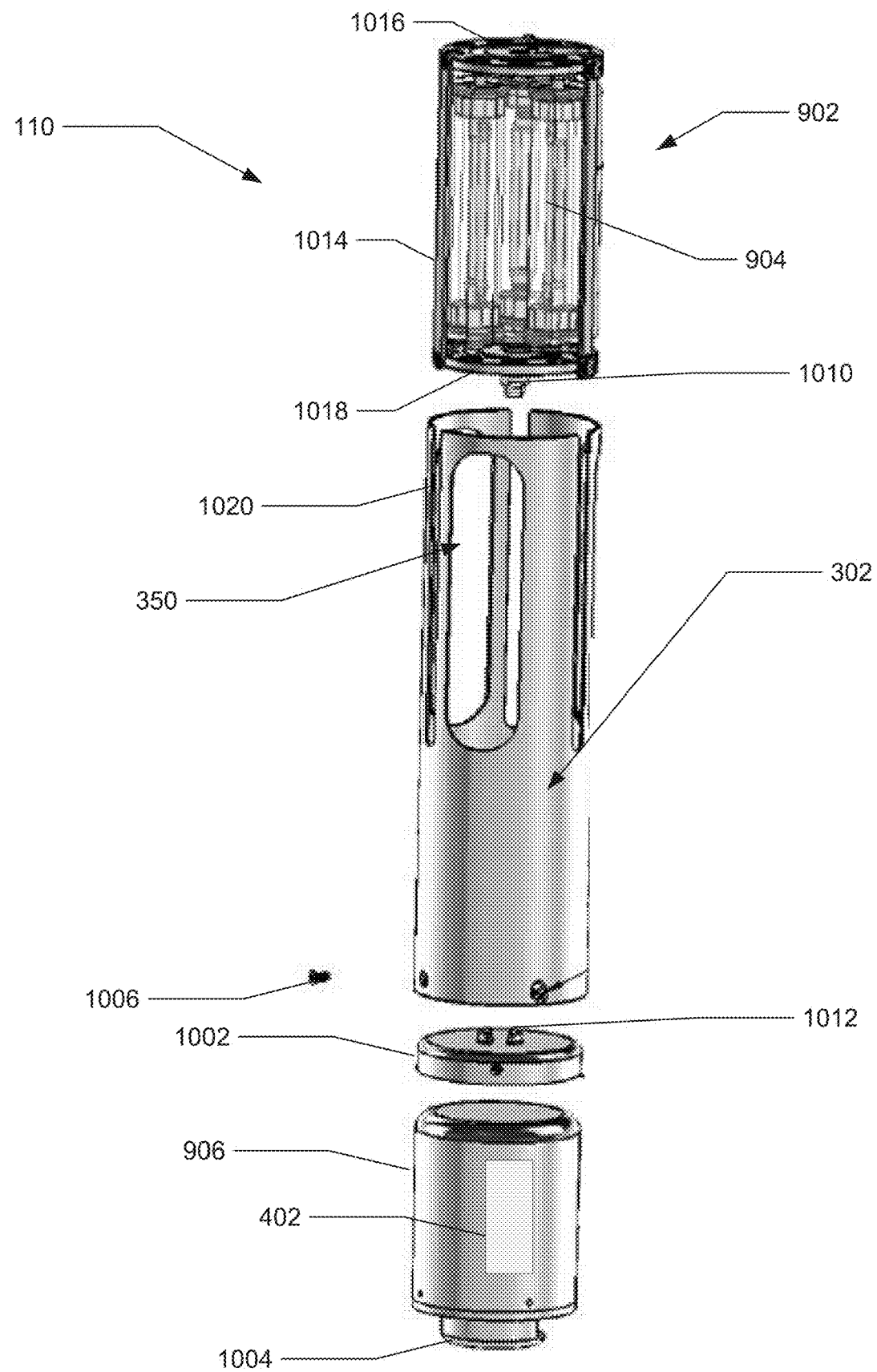
FIG. 10 shows a diagram of an assembly view of the sampling container of FIG. 9, according to an embodiment of the present disclosure.

FIG. 10 shows an assembly view of the sampling container 110 of FIG. 9. Similar to the first embodiment, the sampling container 110 includes the shroud housing 302 including one or more windows 350. Additionally, similar to the first embodiment, the sampling container 110 includes a motor housing and a sample container housing (which are renumbered 902 and 906 respectively). However, the illustrated motor housing 906 and the sample container housing 902 have different assemblies compared to the motor housing 304 and the sample container housing 306 of the first embodiment shown in FIGS. 3 to 8.

In the illustrated embodiment, the motor housing 906 uses magnetic coupling to rotate the sample container housing 902. The motor housing 906 includes the motor 402, which rotates a drive shaft connected to a plate containing at least one magnet. Rotation of the drive shaft causes the plate to rotate, thereby rotating the at least one magnet around the drive shaft. A magnetic plate 1002 contains at least one magnet that magnetically couples with a corresponding magnet in the motor housing 906. The magnet in the magnetic plate 1002 is fixed such that rotation of the magnet in the motor housing 906 causes the magnetic plate 1002 to likewise rotate (e.g., rotate in unison) while remaining in contact with the motor housing 906.

The magnetic plate 1002 and the motor housing 906 are configured to be enclosed by the shroud housing 302, as illustrated in FIG. 9. In some embodiments a bottom side of the motor housing 906, including a wire cap 1004, may be located outside of the shroud housing 302 or otherwise exposed. Wires from the control electronics 114 of the ROV 100 may electrically connect to the motor 402 through the wire cap 1004.

The example motor housing 906 is connected to the shroud housing 302 via one or more connectors 1006. As shown in FIG. 10, the connector 1006 may include a screw or other fastener to secure the motor housing 906 to the shroud housing 302. The connector 1006 prevents the motor housing 906 from rotating by being fixed to the shroud housing 302, which may be retained in place by the connection mechanism 120 of FIG. 1 or other similar mechanical coupling.

Figure 11:
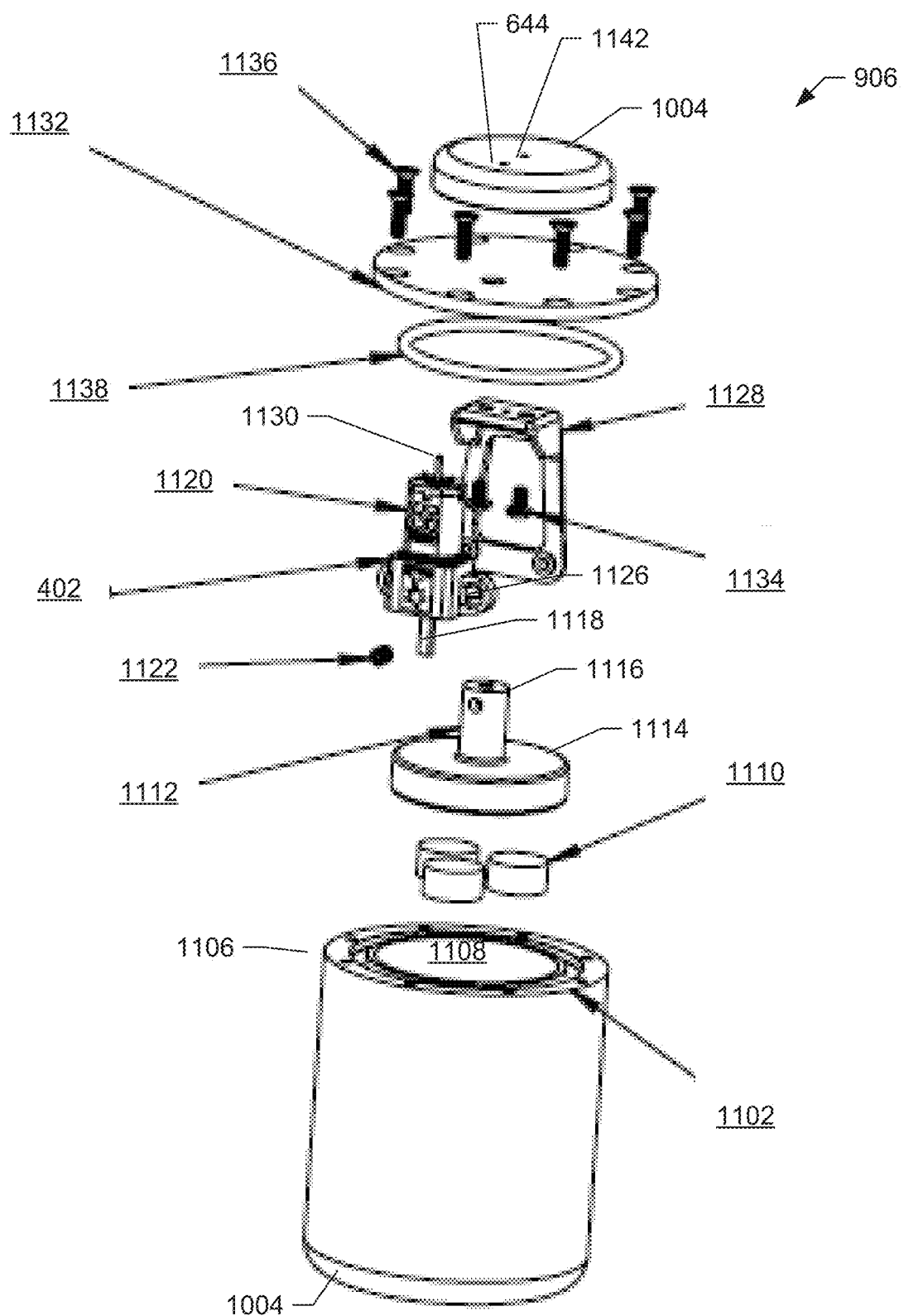
FIG. 11 shows a diagram of an assembly view of a motor housing of the sampling container of FIGS. 9 and 10, according to an example embodiment of the present disclosure.

FIG. 11 shows a diagram illustrating an assembly view of the motor housing 906 of FIGS. 9 and 10, according to an example embodiment of the present disclosure. The example motor housing 906 includes a connector cup 1102 configured to connect to the shroud housing 302. In some embodiments, the connector cup 1102 has a diameter that is substantially the same as the shroud housing 302. The diameter is between an inch and twelve includes, preferably, between two and four inches. The connector cup 1102 includes a closed end 1004 that is configured to contact the magnetic plate 1002. The connector cup 1102 also includes an open end 1106 configured to expose an interior section 1108.

The example motor housing 906 also includes one or more magnets 1110 that are located at the closed end 1004 of the connector cup 1102. The one or more magnets 1110 are held in place or secured by a magnet plate 1112. The example magnet plate 1112 includes a cylindrical-shaped magnet end 1114 that includes recess sections to accommodate the magnets 1110. The diameter of the cylindrical-shaped magnet end 1114 may be substantially equal to a diameter of the interior section 1108 of the connector cup 1102. The magnet plate 1112 also includes a cylindrical-shaped motor end 1116 configured to connect to a drive shaft 1118 of a motor assembly 1120. A socket screw 1122 may be used to secure the drive shaft 1118 to the cylindrical-shaped motor end 1116. Additionally, setscrews may be used to secure the magnets 1110 within the magnet plate 1112. In an example, each magnet 1110 may be secured by a respective setscrew within the magnet plate 1112. The setscrews may firmly position the magnets 1110 within the magnet plate 1112 to reduce or eliminate movement and/or vibration of the magnets 1110 during rotation. While the illustrated embodiment shows three magnets 1110, it should be appreciated that the magnet plate 1112 may contain only one magnet or as many as twenty (or more) magnets.

The example motor assembly 1120 includes a motor 402 configured to rotate the drive shaft 1118. The motor assembly 1120 also includes a bracket connector 1126 configured to mechanically couple to bracket 1128 via respective screws. The motor assembly 1120 further includes a reference shaft 1130 that is configured to provide an indication of a rotation of the drive shaft 1118. An encoder may be connected to the reference shaft 1130 to determine rotation of the drive shaft 1118 to provide rotational feedback control. The encoder may be a mechanical encoder, optical encoder, magnetic encoder, capacitive encoder, etc.

In some embodiments, data from the encoder may be transmitted to an operator to indicate an amount of rotation of the sample container housing 902. The amount of rotation may also be used to determine which interior chambers or tanks of the sample container housing 902 have been sealed.

The example motor assembly 1120 of FIG. 11 is secured to the connector cup 1102 via the bracket 1128, which is connected to a coupling cover 1132 via one or more screws 1134. The coupling cover 1132 is configured to connect to the open end 1106 of the connector cup 1102 to enclose the interior section 1108. Screws 1136 may secure the coupling cover 1132 to the connector cup 1102. In some embodiments, an o-ring 1138 may be located within a channel at the open end 1106 and contact a circular section of the coupling cover 1132. The o-ring 1138 may, for example, create a watertight barrier to prevent water from entering the interior section 1108.

The example motor housing 906 further includes the wire cap 1004, which is mechanically coupled to the coupling cover 1132. The wire cap 1004 includes at least one window to enable wires from the control circuitry 114 of the ROV 100 to be routed to circuit boards within the interior section 1108. The coupling cover 1132 may also include at least one window to enable wires to pass through. A perimeter of the windows of the coupling cover 1132 and the wire cap 1004 may include an o-ring or sealant to prevent water from entering along the wires. In some embodiments, a center of the wire cap 1004 may include a first window 1142 configured to allow a first wire to pass through and a second window 1144 configured to allow a second wire to pass through. The wires may be connected to the control electronics 114b passing through the body 152 of the ROV 100.

The example wire cap 1004, the coupling cover 1132, and/or the connector cup 1102 may comprise any material including, for example, machined metal, injection molded metal, machined plastic, injection molded plastic (e.g., thermoplastic), fiberglass, carbon fiber, etc. Further, while the wire cap 1004, the coupling cover 1132, and/or the connector cup 1102 are shown as having a circular or cylindrical shape, it should be appreciated that they could include other shapes, such as an ovular shape, a rectangular shape, a triangular shape, etc.

Returning to FIG. 10, the example sample container housing 902 includes a tab 1010 configured to connect to the magnetic plate 1002. The tab 902 may include, for example, the connector 410 shown and described in connection with FIG. 4. In some embodiments, the tab 902 may contact or enclose a hex nut 1012 positioned on the magnetic plate 1002. In an example, the hex nut 1012 is located in a center of the magnetic plate 1002 such that the hex nut 1012 rotates along an axis of the drive shaft 1118 of the motor 402. Rotation of the hex nut 1012 causes the tab 902 to rotate, thereby rotating the sample container housing 902. The tab 1010 is configured to be releasable connected to the magnetic plate 1002. The releasable connection enables the sample container housing 902 to be removed from the shroud housing 302.

The example sampling container 110 of FIG. 10 includes at least one support beam 1014 to connect retainer plates 1016 and 1018. The support beam 1014 is similar to the support beam 450 discussed in connection with FIG. 4. Together, the support beam(s) 1014 and the retainer plates 1016 and 1018 encompass or enclose the sample container housing 902. The support beam(s) 1014 are configured to engage or otherwise slide into respective channels 1020 of the shroud housing 302 (as shown in FIG. 9). One or more screw connectors (e.g., connectors 910 shown in FIG. 9) may be used to connect the support beam 1014 and/or the retainer plate 1016/1018 to the shroud housing 302. Placement of the support beam(s) 1014 within the respective channels 1020 prevents the retainer plates 1016 and 1018 from rotating with the sample container housing 902. Further, the connection of the support beam(s) 1014 and/or the retainer plates 1016 and 1018 to the shroud housing 302 using the connectors 910 secures the sample container housing 902 within the shroud housing 302.

In some embodiments, the connector 910 may connect the support beam(s) 1014 to the retainer plates 1016 and 1018. In these embodiments, the sample container housing 902 and the retainer plates 1016 and 1018 may be connected to the shroud housing 302 via a connection force between the support beam(s) 1014 and respective channels 1020 that is sufficient to secure the sample container housing 902 and the retainer plates 1016 and 1018 to the shroud housing 302. Additionally or alternatively, one or more retaining clips or connectors may be used to secure the sample container housing 902 and the retainer plates 1016 and 1018 to the shroud housing 302.

Figure 12:
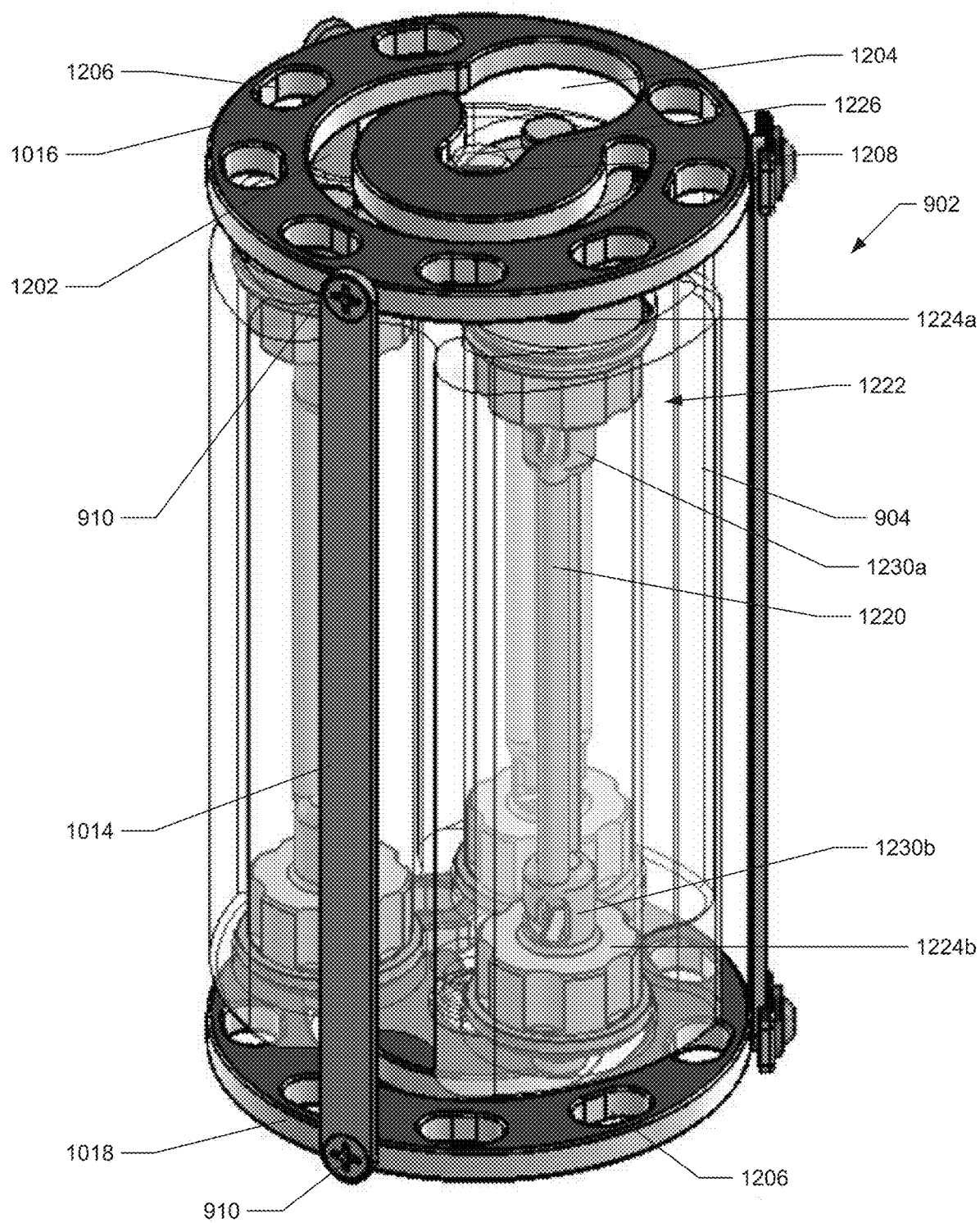
FIG. 12 shows a diagram of a perspective view of a sample container housing of the sampling container of FIGS. 9 and 10, according to an example embodiment of the present disclosure.
Figure 13:
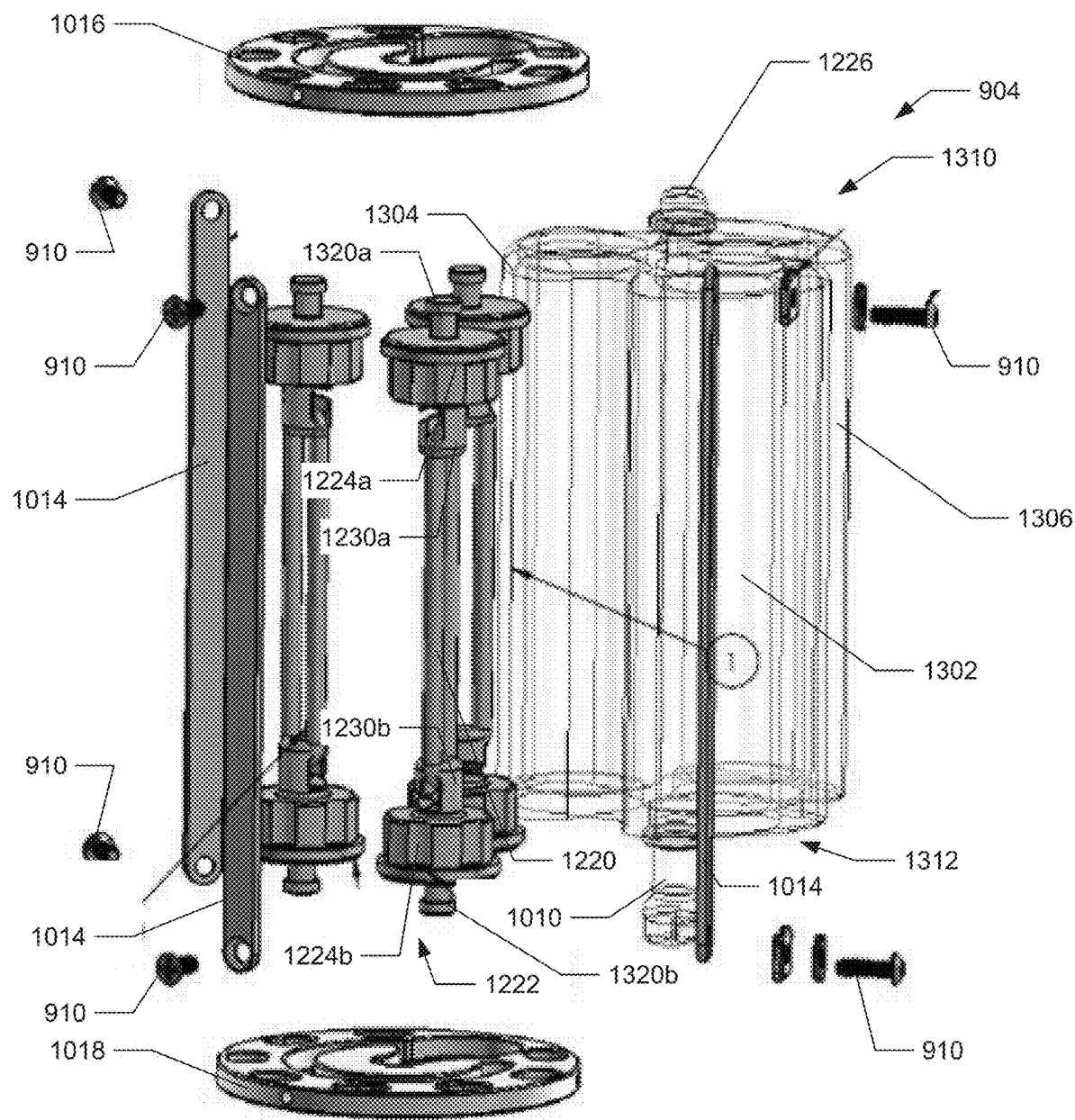
FIG. 13 shows a diagram of an assembly view of the sample container housing of FIG. 12, according to an example embodiment of the present disclosure.

FIG. 12 shows a diagram of a perspective view of the sample container housing 902 of FIGS. 9 and 10 enclosed by the support beam(s) 1014 and the retainer plates 1016 and 1018, according to an example embodiment of the present disclosure. In addition, FIG. 13 shows an assembly view of the sample container housing 902, the support beam(s) 1014, and the retainer plates 1016 and 1018, according to an example embodiment of the present disclosure.

Figure 14:
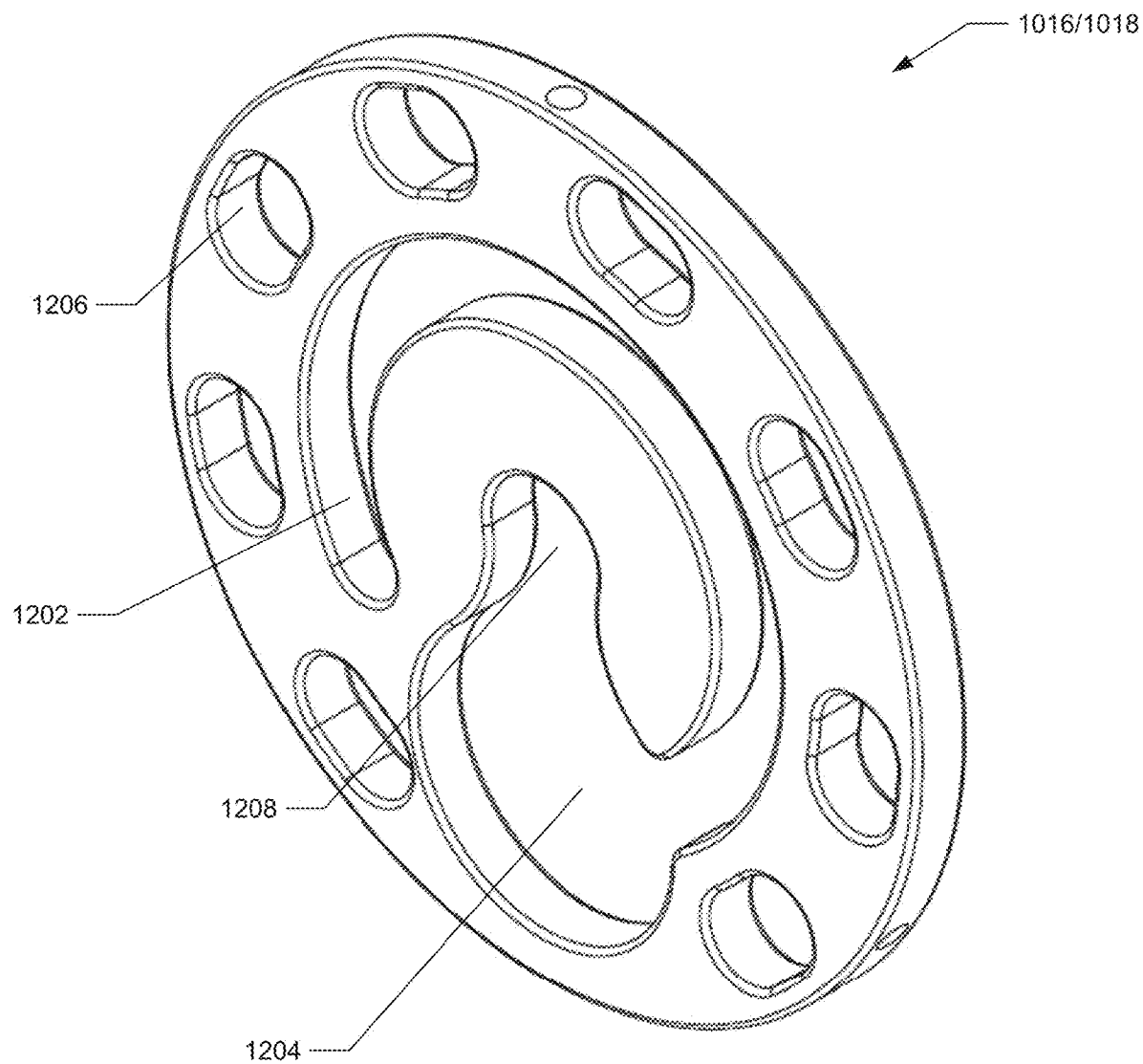
FIG. 14 shows a diagram of a retainer plate of the sampling container of FIGS. 9 to 13, according to an example embodiment of the present disclosure.

The example retainer plates 1016 and 1018 (additionally shown in FIG. 14) are similar to the retainer plates 440 and 442 of FIG. 4. For instance, the retainer plates 1016 and 1018 each include a travel channel 1202 and a plunger window 1204. The illustrated retainer plates 1016 and 1018 also include one or more cutout 1206 that is located between the travel channel 1202 and a circumference of the plates 1016 and 1018. The cutout(s) 1206 are configured to enable a sample (e.g., a fluid) to pass through to reach the tank 904 of the sample container housing 902. While the cutout(s) 1206 are shown as having an oval-shape, in other embodiments the cutout(s) 1206 may have a round-shape, a rectangular-shape, a triangular-shape, etc. Further, while FIGS. 12 to 14 show eight cutouts 1206, other examples may include fewer cutouts or additional cutouts. It should also be appreciated that the scale of the cutouts 1206 may be different in other embodiments. For example, the cutouts 1206 may be larger or smaller. Moreover, in some embodiments, the cutouts 1206 may comprise one or more channels in parallel with the travel channel 1202.

The example travel channel 1202 defines an opening or space within the retainer plates 1016 and 1018 and is configured to have a diameter that is greater than a shaft 1220 of a plunger 1222 but less than a diameter of a cup 1224 of the plunger 1222. The diameter of the travel channel 1202 permits the shaft 1220 to pass through during rotation of the sample container housing 902 while retaining or holding the plunger 1222 in an open position by preventing the cup 1224 (or a portion thereof) from passing through. The travel channel 1202 is positionally aligned with the one or more plungers 1222 of the sample container housing 902, as shown in FIGS. 12 and 13. Further, the travel channel 1202 includes a curved shape that matches a path of travel of the plungers 1222 during rotation of the sample container housing 902.

The example plunger window 1204 defines an opening at an end of the travel channel 1202. A portion of the plunger window 1204 is connected to the travel channel 1202, which enables a plunger 1222 (or a portion thereof) to move from the travel channel 1202 to the plunger window 1204 during rotation. The plunger window 1204 has a diameter that is larger than the diameter of the cup 1224 (or a top portion of the cup), thereby enabling the cup 1224 (or the top portion of the cup) to pass through.

The example retainer plates 1016 and 1018 may also include a retaining cutout 1208 configured to engage a respective tab 1010 and 1226 of the sample container housing 902. The retaining cutout 1208 defines an opening for the respective tab 1010 and 1226 to contact or pass through while enabling the sample container housing 902 to rotate. The retaining cutout 1208 secures or otherwise positions the sample container housing 902 with the retainer plates 1016 and 1018 to align the plungers 1222 with the travel channel 1202. The connection between the retaining cutout 1208 and the tabs 1010 and 1226 also prevents the sample container housing 902 from rattling or otherwise coming loose in an underwater environment.

The example tank 904 of the sample container housing 902 of FIGS. 12 and 13 is configured to fit between the retainer plates 1016 and 1018. The illustrated tank 904 is shown as comprising a transparent material, such as plastic or glass. The transparency of the tank 904, enables, for example, an operator to view contents of the tank 904 without opening or exposing the contents to the air. In other examples, the tank 904 includes an opaque material or paint.

Figure 15:
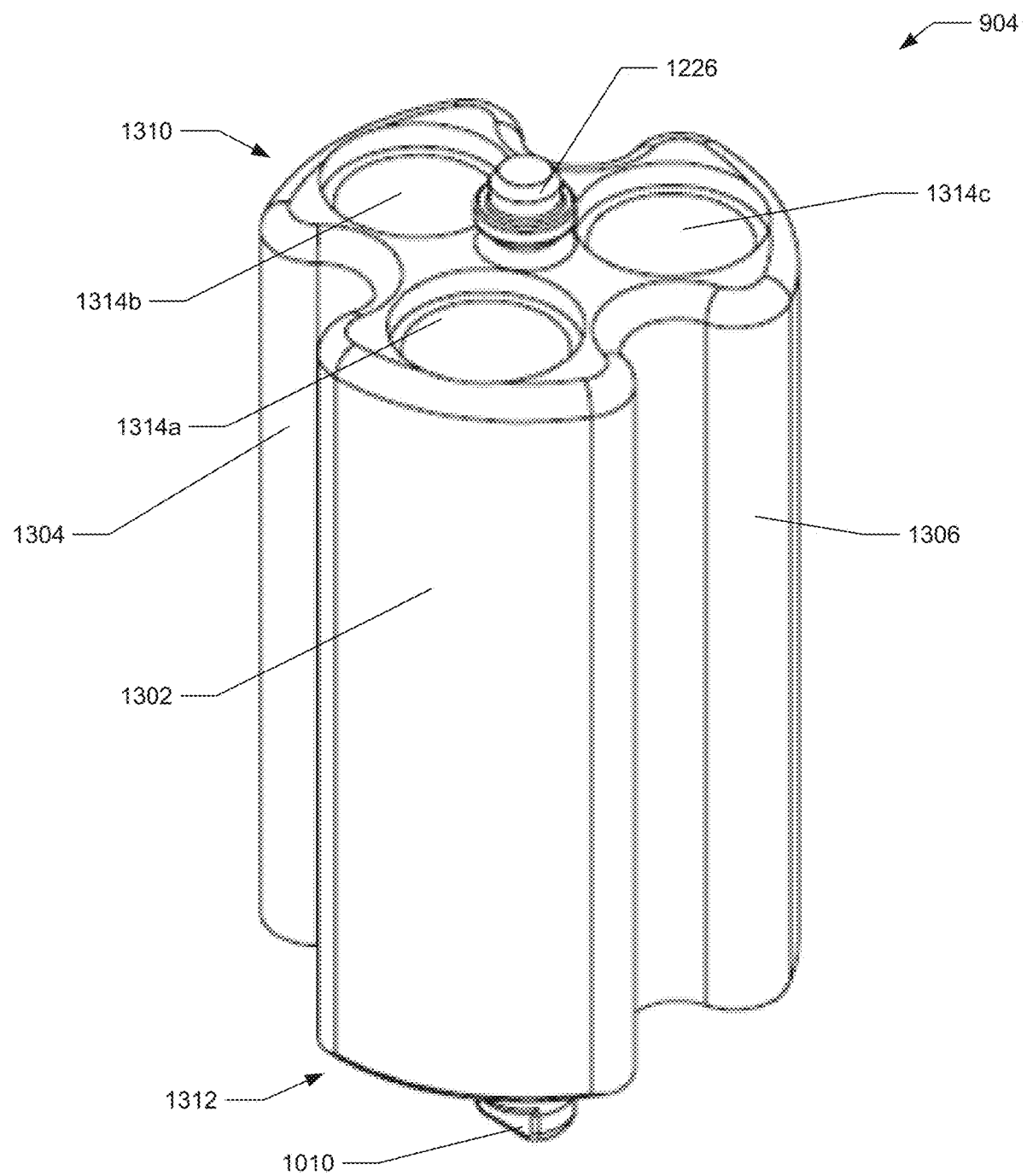
FIG. 15 shows a diagram of a tank of the sample container housing of FIGS. 9 to 13, according to an example embodiment of the present disclosure.

FIGS. 13 and 15 show a diagram of the tank 904 of FIGS. 9, 10, 12, and 13, according to an example embodiment of the present disclosure. The illustrated tank 904 includes three separate interior chambers 1302, 1304, and 1306. The chambers 1302, 1304, and 1306 are configured to enclose or otherwise contain one or more collected samples. While the chambers 1302, 1304, and 1306 are shown as being separated, in other embodiments, the chambers may be fluidly connected together. For example, tank 904 may include interior passageways or channels between the chambers 1302, 1304, and 1306. Alternatively, the chambers 1302, 1304, and 1306 may be combined together to form one chamber in the tank 904.

While the tank 904 is shown as having three chambers 1302, 1304, and 1306, in other examples the tank 904 may contain fewer or additional chambers. Moreover, while the chambers 1302, 1304, and 1306 have a generally circular-profile, in other examples, the chambers may comprise other profiles, such as a rectangular profile.

The example tank 904 of FIGS. 12, 13, and 15 is connected to or integrally formed with tabs 1010 and 1226. As discussed above, the tabs 1010 and 1226 contact respective retainer cutouts 1208 in the retainer plates 1016 and 1018 to secure the sample container housing 902. In addition, tab 1010 is configured to connect to the magnetic plate 1002. The tabs 1010 and 1226 are located on an axis of rotation of the tank 904 to provide even, steady, secure rotation.

As shown in FIGS. 13 and 15, the example tank 904 (or more generally, the sample container housing 902) includes a first end 1310 and a second end 1312 each having three openings 1314 or windows. The openings 1314 are more easily viewable in FIG. 15. The first end 1310 of the tank 904 includes tab 1226 and is positioned adjacent to the retainer plate 1016. The second end 1312 of the tank 904 includes tab 1010 and is positioned adjacent to the retainer plate 1018. The openings 1314 define spaces in the first end 1310 and the second end 1312 of the tank 904 for one or more samples to pass through and correspond to interior chambers 1302, 1304, and 1306. For example, FIG. 15 shows the first end 1310 of the tank 904 having a first opening 1314a aligned with interior chamber 1302, a second opening 1314b aligned with interior chamber 1304, and a third opening 1314c aligned with interior chamber 1306. In addition, the openings 1314 of the first end 1310 are aligned with the openings 1314 of the second end 1312 to enable fluid to pass through the respective interior chambers 1302, 1304, and 1306. In other words, each of the interior chambers 1302, 1304, and 1306 includes an opening 1314 at each end.

In alternative embodiments, the tank 904 may include openings 1314 at only one of the first end 1310 or the second end 1312. Additionally or alternatively, while the openings 1314 and interior chambers 1302, 1304, and 1306 are shown as being cylindrical or having a circular-profile, in other examples, the tank 904 may include an interior chamber similar to chamber 424 of FIG. 4 and include one or more channels 428 that fluidly connect to openings 426 (i.e., container windows).

Returning to FIGS. 12 and 13, the example sample container housing 902 includes a plunger 1222 for each of the interior chambers 1302, 1304, and 1306. As discussed above, each of the plungers 1222 includes a shaft 1220, a first cup 1224a, and a second cup 1224b. The cups 1224 are located at opposite ends of the shaft 1220 and configured to cover or seal respective openings 1314 in one of the interior chambers 1302, 1304, and 1306. In some embodiments, the cups 1224 are integrally formed with the shaft 1220. In other embodiments, the shaft 1220 is mechanically connected to the cups 1224. For example, FIGS. 12 and 13 show the shaft 1220 as an elastic band that is placed around hooks 1230 of the cups 1224a and 1224b. In other examples, the shaft 1220 may include a spring that is placed around a tab of the cups 1224, where the tab replaces the hook 1230. In yet other examples, the shaft 1220 may include a magnetic or mechanical constriction mechanism or a retraction mechanism that is connected to the cups 1224 via a mechanical fastener (e.g., a screw), a chemical fastener (e.g., an adhesive), or a weld.

The example shafts 1220 are located within respective chambers 1302, 1304, and 1306 and configured to provide a constriction or retraction force for each of the cups 1224. The constrictive force provided by the shaft 1220 causes the cups 1224 to be pulled toward a center of the respective interior chamber 1302, 1304, and 1306. In some embodiments, each cup 1224 may have a separate shaft 1220, where an interior end of the shaft is connected to an interior portion of the respective interior chamber 1302, 1304, and 1306. In embodiments where the tank 904 includes only one side with openings 1314, an end of the shaft 1220 that is opposite the cup 1224 (e.g., the interior end of the shaft 1220) is connected to an interior portion of the interior chamber 1302, 1304, and 1306.

Figure 16:
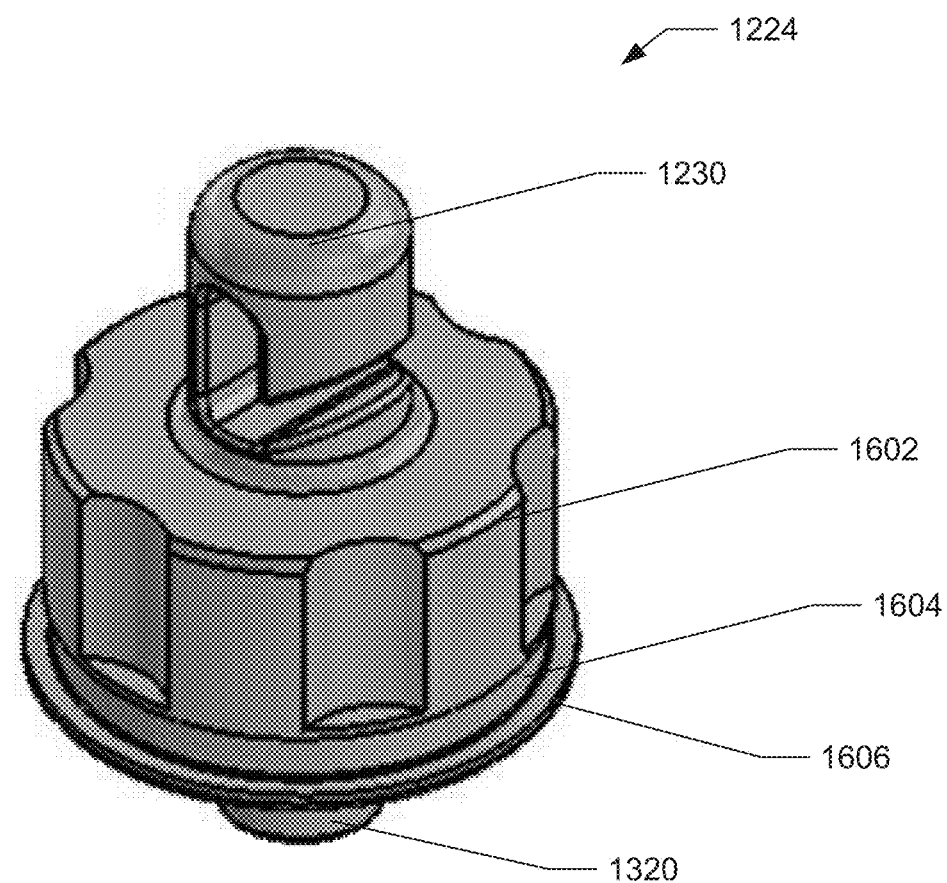
FIG. 16 shows a diagram of a cup of a plunger of the sample container housing of FIGS. 9 to 13, according to an example embodiment of the present disclosure.

The example cups 1224 are configured to create a seal or water-tight connection with a respective opening 1314 of the tank 904. FIG. 16 shows a diagram illustrating an example embodiment of the cup 1224. As mentioned above, the cup 1224 includes a hook 1230 (or other connector) configured to connect to the shaft 1220. The cup 1224 also includes a body 1602 and a seal 1604. The example body 1602 is dimensioned to fit within the opening 1314 of the tank 904 and an end of the interior chamber 1302, 1304, or 1306. The example seal 1604 is configured to engage or otherwise contact the opening 1314 of the tank 904 to create a watertight interface. The body 1602 provides structural support for the seal 1604 from forces applied by the shaft 1220 via the hook 1230. In some embodiments, the body 1604 may comprise a hard plastic or metal while the seal 1604 includes a compressible plastic, rubber, or derivations thereof. The illustrated seal 1604 includes a lip 1606 that has a diameter slightly larger than the opening 1314 to cover the opening 1314, thereby creating a secure connection as the cup 1224 receives a pulling force toward the interior chamber 1302, 1304, and 1306.

The example cup 1224 also includes a travel tab 1320 (shown in FIGS. 13 and 16), which is configured to pass through the travel channel 1202 of the respective retainer plate 1016 and 1018. The travel tab 1320 includes a first end that is connected to the seal 1604 of the cup 1224. A second end of the travel tab 1320 has a diameter that is larger than a mid-section of the tab 1320 and is configured to engage the travel channel 1202. The diameter of the second end of the tab 1320 is also greater than the diameter of the travel channel 1202. Accordingly, the second end of the travel tab 1320 is configured to be retained or rest on top of the travel channel 1202 to keep the plunger 1222 in the open position. The diameter of the second end of the travel tab 1320 is less than a diameter of the plunger window 1204, which enables the second end to pass through the plunger window 1204 when the travel tab 1320 reaches the plunger window 1204 during rotation of the sample container housing 902. Accordingly, the passing of the travel tab 1302 through the plunger window 1204 enables the plunger to actuate from an open position to a closed position causing the cup 1224 to create a seal with a respective opening 1314 of the tank 904.

Mounting Location Embodiment

Figure 17:
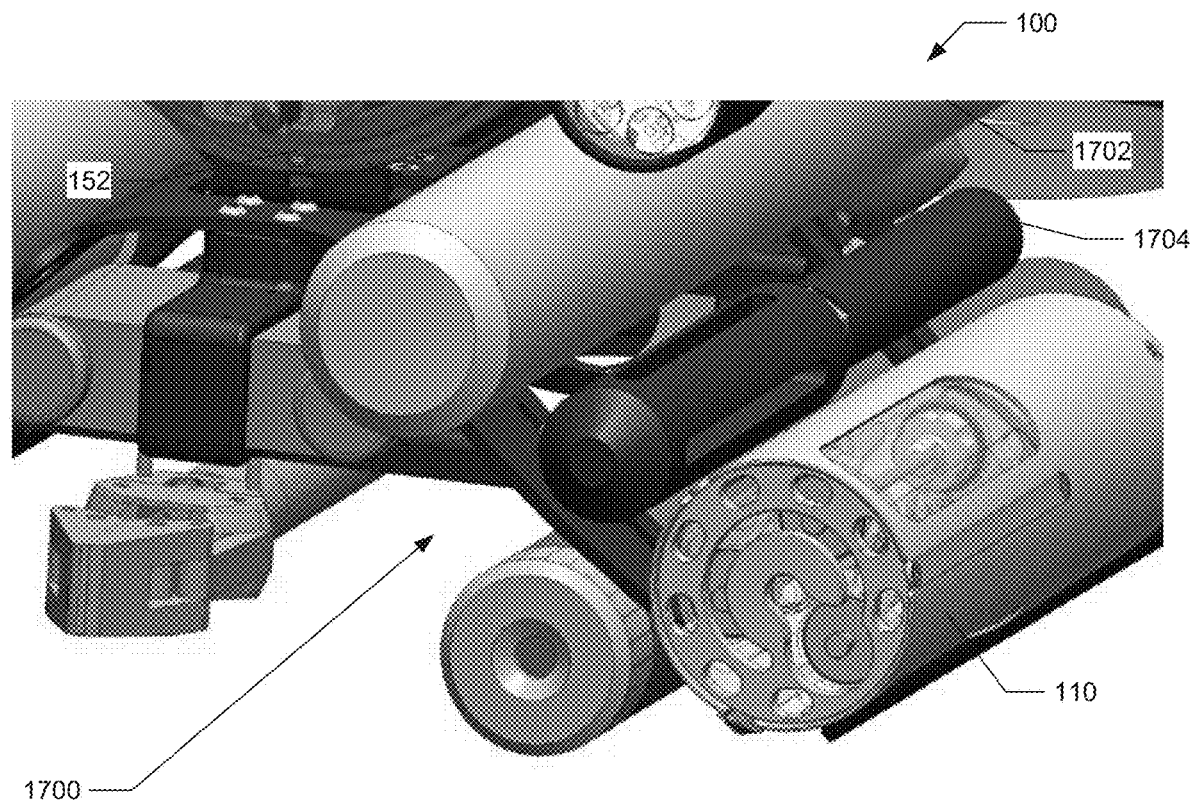
FIG. 17 shows a diagram illustrating the sampling container mounted to an appendage of the ROV of FIGS. 1 and 2.

FIGS. 1 and 2 illustrate the example sampling container 110 mounted to the body 152 of the ROV 100. FIG. 17 shows a diagram illustrating the sampling container 110 mounted to an appendage 1700 of the ROV 100. The example appendage 1700 is connected to the body 152 and may include the landing gear 160 shown in FIGS. 1 and 2. As illustrated, the appendage 1700 includes slots or connectors that enable different modules to be attached. For example, modules 1702 and 1704 may comprise sensors, navigational aids, weights, etc. The module also includes the sampling container 110 for collecting one or more samples. The sampling container 110 is coupled to a connection mechanism, which connects to the appendage 1700.

Example Operation of the First and Second Embodiment of the Sampling Container

Figure 18:
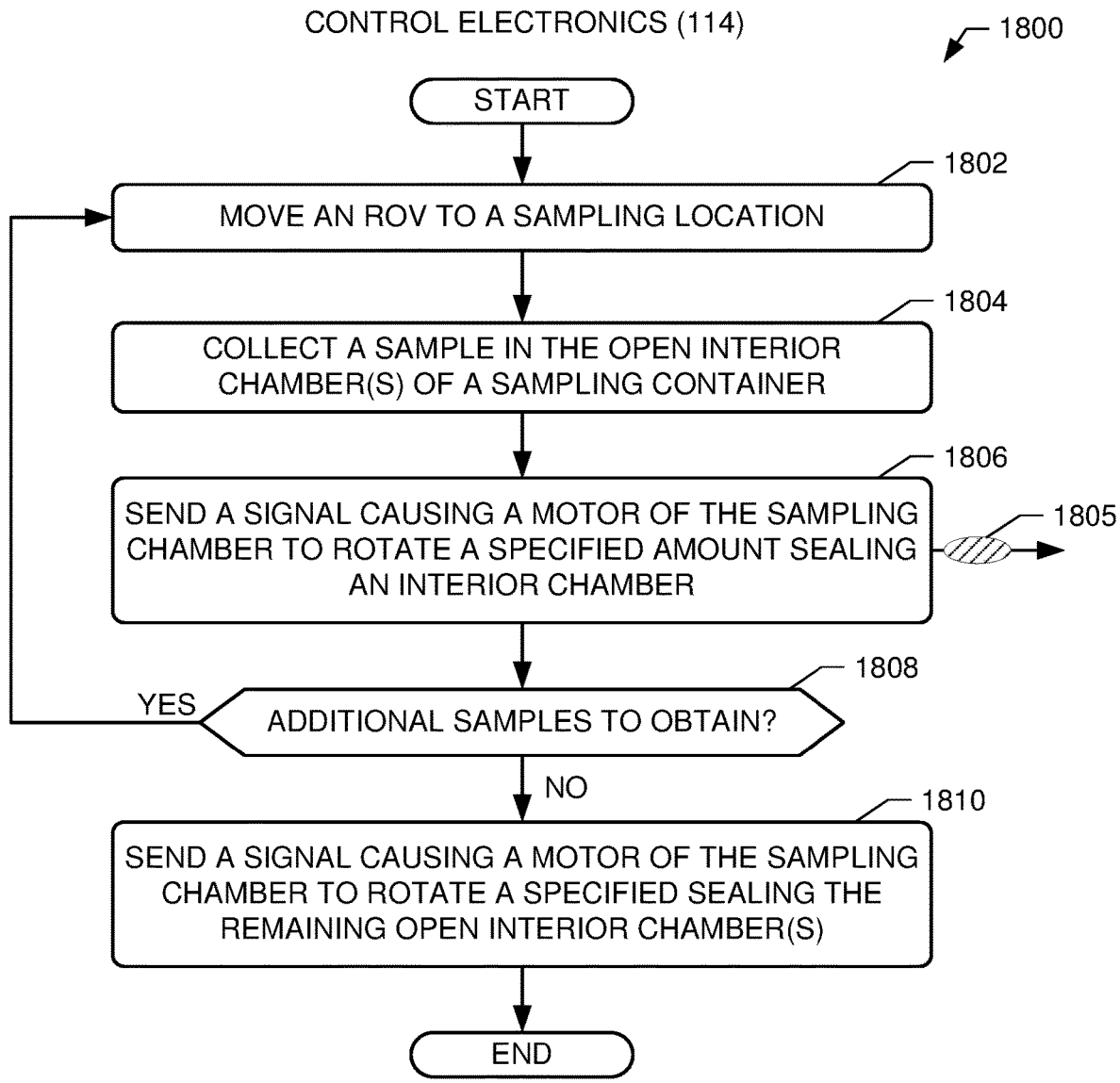
FIG. 18 illustrates a flow diagram showing an example procedure to collect one or more samples using the example sampling container of FIGS. 1 to 17, according to an example embodiment of the present disclosure.

FIG. 18 illustrates a flow diagram showing an example procedure 1800 to collect one or more samples using the sampling container 110 of FIGS. 1 to 17, according to an example embodiment of the present disclosure. Although the procedure 1800 is described with reference to the flow diagram illustrated in FIG. 18, it should be appreciated that many other methods of performing the steps associated with the procedure 100 may be used. For example, the order of many of the blocks may be changed, certain blocks may be combined with other blocks, and many of the blocks described are optional. For example, in some embodiments, samples are collected in one location such that the interior chambers of the sampling container 110 are sealed at the same time.

The example procedure 1800 of FIG. 18 operates on, for example, the control electronics 114 of the ROV 100. The procedure 1800 begins when the ROV 100 is moved to an underwater location to collect one or more samples (block 1802). Next, at the location, one or more samples are collected in the interior chambers of the sample container housing of the sampling container 110 (block 1804). In some embodiments, samples are collected by enabling water or another fluid to pass through the open interior chambers. In other embodiments, a robotic arm or other device deposits the one or more samples into the sampling container 110.

After the sample is collected, the control electronics 114 send one or more signals 1805 to the motor 402 of the sampling container 110 causing the sample container housing to rotate a specified amount (block 1806). The signal 1805 may specify, for example, that the motor 402 is to rotate 60 degrees causing one plunger of the sample container housing to actuate from an open position to a closed position, thereby sealing one or more open ends of one of the interior chambers. It should be appreciated that rotation of 30 to 90 degrees is sufficient to move the plunger through a travel channel of a retainer plate to a plunger window, enabling a cup (or a portion of the cup) of the plunger to pass through. An additional 30 to 90 degrees of rotation by the motor 402 may be sufficient to move a second plunger to the plunger window, thereby causing a second plunger to actuate to a closed position.

After at least one interior chamber is sealed, the control electronics 114 determine whether additional samples are to be obtained (block 1808). This step may include the control electronics 114 receiving instructions from an operator to move the ROV 100 to another location for sample collection. If there are additional samples, the procedure 1800 returns to block 1802 for collection of the next sample in the interior chambers that remain open. It should be appreciated that the open interior chambers enable any previous sample to be flushed out through movement of the ROV 100 and/or water currents to enable a next sample to be collected.

If there are no additional samples to collect, the example procedure 1800 may send one or more signals to the motor 402 of the sampling container 110 causing the sample container housing to rotate a specified amount (block 1810). The signals cause the sampling container 110 to rotate a specified amount closing or sealing the remaining open interior chambers. The procedure 1800 then ends. At this point, the sampling container 110 contains one or more collected samples sealed in one or more interior chambers. After the ROV 100 is brought to the surface, an operator may open the interior chambers to access the samples. Further, the operator may return the plungers to an open position to prepare the sampling container 110 for another mission.

Conclusion

It will be appreciated that each of the systems, structures, methods and procedures described herein may be implemented using one or more computer program or component. These programs and components may be provided as a series of computer instructions on any conventional computer-readable medium, including random access memory ("RAM"), read only memory ("ROM"), flash memory, magnetic or optical disks, optical memory, or other storage media, and combinations and derivatives thereof. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Moreover, consistent with current U.S. law, it should be appreciated that 35 U.S.C. 112(f) or pre-AIA 35 U.S.C. 112, paragraph 6 is not intended to be invoked unless the terms "means" or "step" are explicitly recited in the claims. Accordingly, the claims are not meant to be limited to the corresponding structure, material, or actions described in the specification or equivalents thereof.

What is claimed is:

1. A sampling container apparatus comprising:
   a motor housing comprising a motor configured to rotate at least one magnet around a drift shaft of the motor;
   a magnetic plate configured to magnetically couple to the at least one magnet of the motor housing, the magnetic plate configured to rotate in unison with the at least one magnet of the motor housing;
   a shroud housing configured to enclose at least some of the motor housing and the magnetic plate;
   a sample container housing configured to be placed within the shroud housing and mechanically connected to the magnetic plate, the sample container housing including
      a tank configured to hold a sample within an interior chamber, the tank including a first end having a first opening to the interior chamber and a second end having a second opening to the interior chamber, and
      a plunger having a shaft positioned within the interior chamber, the plunger having a first cup at a first end configured to seal the first opening of the tank and a second cup at a second end configured to seal the second opening of the tank, the shaft connected to the first end and the second end of the plunger and configured to pull the first end and second end of the plunger toward each other;
   a first retainer plate located above the first end of the tank, the first retainer plate including
      a first plunger window configured to enable the first cup of the plunger to pass through, and
      a first travel channel connected to the first plunger window, the first travel channel having a width that is larger than the shaft and smaller than the first cup of the plunger; and
   a second retainer plate located below the second end of the tank, the second retainer plate including
      a second plunger window configured to enable the second cup of the plunger to pass through, and
      a second travel channel connected to the second plunger window, the second travel channel having a width that is larger than the shaft and smaller than the second cup of the plunger,
   wherein the first and second retainer plates are configured to retain the plunger in an open position until the sample container housing is rotated by the motor, causing the sample container housing including the plunger to rotate relative to the first and second retainer plates along the first and second travel channels such that the first cup passes through the first plunger window and the second cup passes through the second plunger window when the cups are aligned with the respective windows, thereby enabling the plunger to actuate to a closed position and causing the first cup to seal the first opening of the tank and the second cup to seal the second opening of the tank.

2. The sampling container apparatus of claim 1, further comprising a support beam positioned along a length of the sample container housing and configured to connect the first retainer plate to the second retainer plate.

3. The sampling container apparatus of claim 2, wherein the shroud housing includes a retainer channel configured to accept the support beam to secure the support beam to the shroud housing thereby preventing the first and second retainer plates from rotating.

4. The sampling container apparatus of claim 1, wherein the shroud housing includes at least one window aligned with the tank.

5. The sampling container apparatus of claim 1, wherein at least a portion of the tank includes a transparent material that enables contents of the interior chamber to be visible.

6. The sampling container apparatus of claim 1, wherein the shaft includes at least one of an elastic band and a spring.

7. The sampling container apparatus of claim 1, wherein at least one of the first retainer plate and the second retainer plate includes at least one cutout configured to enable fluid to pass through to the interior chamber.

8. The sampling container apparatus of claim 1, wherein the tank includes three separate interior chambers, each of the three interior chambers including a plunger having a shaft positioned within the respective interior chamber, the plunger having a first cup at a first end configured to seal a first opening of the respective interior chamber and a second cup at a second end configured to seal a second opening of the respective interior chamber, the shaft connected to the first end and the second end of the plunger and configured to pull the first end and second end toward each other.

9. The sampling container apparatus of claim 8, wherein the first and second retainer plates are configured to retain the three plungers in the open position until the sample container housing is rotated by the motor, causing the sample container housing including the three plungers to rotate relative to the first and second retainer plates along the first and second travel channels such that the first cup of each of the plungers sequentially passes through the first plunger window and the second cup of each of the plungers sequentially passes through the second plunger window enabling the plungers to actuate to the closed position causing the first cup to seal the first opening of the respective interior chamber and the second cup to seal the second opening of the respective interior chamber.

10. The sampling container apparatus of claim 9, wherein the motor receives a first signal at a first time causing the motor to rotate the drive shaft a first amount causing one of the three plungers to actuate to the closed position while keeping the other two plungers in the open position.

11. The sampling container apparatus of claim 10, wherein the motor receives a second signal at a second time, after the first time, causing the motor to rotate the drive shaft a second amount causing a second of the three plungers to actuate to the closed position while keeping the remaining plunger in the open position.

12. The sampling container apparatus of claim 1, wherein the tank includes two openings at the first end to the interior chamber, two openings at the second end to the interior chamber, and two separate plungers each having a shaft positioned within the interior chamber, each of the plungers having a first cup at a first end configured to seal the respective opening at the first end of the tank and a second cup at a second end configured to seal the respective opening at the second end of the tank, the shaft connected to the first end and the second end of the respective plunger and configured to pull the first end and second end toward each other.

13. The sampling container apparatus of claim 1, wherein the first cup and the second cup of the first plunger each includes a travel tab configured to engage the travel channel of the respective retainer plate.

14. A sampling container apparatus comprising:
a motor housing comprising a motor configured to rotate a drive shaft;
a sample container housing rotatably connected to the motor housing via the drive shaft and including
a first end connected to the drive shaft of the motor,
a second end located opposite the first end,
an interior tank configured to hold a sample,
a container window located at the second end,
a channel positioned between the container window and the interior tank, and
a spring-loaded plunger having a shaft positioned within the channel and a cup located at an end of the shaft in proximity to the container window;
a retainer plate located above the second end of the sample container housing, the retainer plate including
a plunger window configured to enable the cup of the plunger to pass through, and
a travel channel connected to the plunger window, the travel channel having a width that is larger than the shaft and smaller than the cup of the plunger; and
a shroud housing configured to enclose the motor housing and the sample container housing,
wherein the retainer plate holds the spring-loaded plunger in an open position until the sample container housing is rotated by the motor, causing the sample container housing including the spring-loaded plunger to rotate relative to the retainer plate such that the cup passes through the plunger window enabling the spring-loaded plunger to actuate to a closed position, thereby causing the cup to cover the container window and seal the interior tank.

15. The sampling container apparatus of claim 14, wherein the shroud housing includes at least one window to enable a sample to pass through.

16. The sampling container apparatus of claim 14, wherein the first end of the sample container housing includes a second container window and a second channel positioned between the second container window and the interior tank or a second interior tank, and
wherein the sample container housing includes a second spring-loaded plunger having a shaft positioned within the second channel and a cup located at an end of the shaft in proximity to the second container window.

17. The sampling container apparatus of claim 14, wherein the motor is controlled from a second, remote location from the sampling container apparatus.

18. The sampling container apparatus of claim 14, wherein the spring-loaded plunger contained within the sample container housing is comprised of an elastic band.

19. The sampling container apparatus of claim 14, further comprising a connector configured to removably connect the shroud housing to a hull or appendage of a remote underwater vehicle.

20. The sampling container apparatus of claim 19, wherein the motor is electrically connected to and receives electrical signals from a controller of the remote underwater vehicle.

21. The sampling container apparatus of claim 14, wherein the sample container housing includes three container windows with respective channels fluidly connected to the interior tank, and
wherein the sample container housing includes a spring-loaded plunger for each of the container windows.

22. The sampling container apparatus of claim 21, wherein the sample container housing includes three separate interior tanks, and
wherein each of the three container windows with respective channels is fluidly connected to one of the three interior tanks.

* * * * *